United States Patent
Grundlehner et al.

(10) Patent No.: US 10,061,891 B2
(45) Date of Patent: Aug. 28, 2018

(54) SYSTEM AND METHOD FOR THE ANALYSIS OF BIOPOTENTIAL SIGNALS USING MOTION ARTIFACT REMOVAL TECHNIQUES

(71) Applicant: Stichting IMEC Nederland, Eindhoven (NL)

(72) Inventors: Bernard Grundlehner, Eindhoven (NL); Vojkan Mihajlovic, Eindhoven (NL)

(73) Assignee: Stitching IMEC Nederland, Eindhoven (NL)

( * ) Notice: Subject to any disclaimer, the term of this patent is extended or adjusted under 35 U.S.C. 154(b) by 923 days.

(21) Appl. No.: 14/252,611

(22) Filed: Apr. 14, 2014

(65) Prior Publication Data

US 2014/0309943 A1    Oct. 16, 2014

(30) Foreign Application Priority Data

Apr. 15, 2013   (EP) ..................................... 13163813

(51) Int. Cl.
*G06F 19/00* (2018.01)
*A61B 5/0402* (2006.01)
(Continued)

(52) U.S. Cl.
CPC ........ *G06F 19/321* (2013.01); *A61B 5/04012* (2013.01); *A61B 5/7207* (2013.01); *A61B 5/7264* (2013.01)

(58) Field of Classification Search
CPC . A61B 5/04012; A61B 5/7207; A61B 5/7264; A61B 5/721
See application file for complete search history.

(56) References Cited

U.S. PATENT DOCUMENTS

| | | | |
|---|---|---|---|
| 5,513,649 A | * | 5/1996 | Gevins ................. A61B 5/0476 600/544 |
| 2006/0122476 A1 | | 6/2006 | Van Slyke |

(Continued)

OTHER PUBLICATIONS

Noh, Yun-Hong, et al. "Implementation of Fuzzy-rule based Activity Classification and Optimized Adaptive Filter-set for Wearable ECG Recording", Oct. 2012, International Journal of Multimedia and Ubiquitous Engineering, vol. 7, No. 4. pp. 59-72.*

(Continued)

*Primary Examiner* — Manuel L Barbee
(74) *Attorney, Agent, or Firm* — Knobbe, Martens, Olson & Bear LLP

(57) ABSTRACT

A system and method for the analysis of biopotential signals using motion artifact removal techniques is disclosed. The system includes a motion classification module configured to receive at least one biopotential signal and at least one reference secondary input signal. The motion classification module performs motion artifact classification for determining motion meta-information, comprising a type and/or severity indication about motion phenomena causing artifacts in the biopotential signal. The motion classification module communicates motion meta-information to a motion artifact reduction module configured to remove motion artifacts from the biopotential signal based on the information received from the motion classification module. The system is further configured to evaluate the effectiveness of at least one algorithm used to remove motion artifacts, and generate feedback information between the motion classification module and the motion artifact reduction module to optimize motion artifact classification.

21 Claims, 19 Drawing Sheets

(51) Int. Cl.
*A61B 5/00* (2006.01)
*A61B 5/04* (2006.01)

(56) References Cited

U.S. PATENT DOCUMENTS

2011/0257555 A1* 10/2011 Banet .................. A61B 5/0809
 600/538
2013/0030711 A1 1/2013 Korhonen

OTHER PUBLICATIONS

Noh, Yun-Hong, et al. "Implementation of Fuzzy-rule based Activity Classification and Optimized Adaptive Filger-set for Wearable ECG Recording", Oct. 2012, International Journal of Multimedia and Ubiquitous Engineering, vol. 7, No. 4, pp. 59-72.*

Kim Hyejung, et al., Motion Artifact Removal using Cascade Adaptive Filtering for Ambulatory ECG Monitoring System, Proc. BioCAS 2012.
Li, Huaming, et al., Body sensor network based context aware QRS detection, Conf Proc IEEE Eng Med Biol Soc. 2006;1:3266-9.
Noh, Yun-Hong, et al., Implementation of Fuzzy-rule based Activity Classification and Optimized Adaptive Filter-set for Wearable ECG Recording, International Journal of Multimedia and Ubiquitous Engineering, vol. 7, No. 4, Oct. 2012.
Shiavi, Richard, Introduction to Applied Statistical Signal Analysis, Elsevier Inc., 3rd edition, San Diego, 2006.
Sweeney, Kevin T., et al., Artifact Removal in Physiological Signals—Practices and Possibilities, IEEE Trans Inf Technol Biomed. May 2012;16(3):488-500.
Sweeney, Kevin T., et al., Intelligent artifact classification for ambulatory physiological signals, $32^{nd}$ Annual International Conference of the IEEE EMBS, Buenos Aires, Argentina, Aug. 31-Sep. 4, 2010, Conf Proc IEEE Eng Med Biol Soc. 2010:6349-52.

* cited by examiner

SYSTEM AND METHOD FOR THE ANALYSIS OF BIOPOTENTIAL SIGNALS USING MOTION ARTIFACT REMOVAL TECHNIQUES

INCORPORATION BY REFERENCE TO RELATED APPLICATIONS

Any and all priority claims identified in the Application Data Sheet, or any correction thereto, are hereby incorporated by reference under 37 CFR 1.57. This application claims the benefit of European Application No. EP 13163813.2 filed on Apr. 15, 2013. The aforementioned application is incorporated by reference herein in its entirety, and is hereby expressly made a part of this specification.

BACKGROUND OF THE INVENTION

Field of the Invention

The present invention relates generally to the field of biopotential signal analysis, e.g., detecting, monitoring and/or processing electrocardiogram (ECG), electroencephalogram (EEG) or electromyography (EMG) signals. More specifically the invention relates to a system and a method for the analysis of such biopotential signals using motion artifact removal techniques.

Description of the Related Art

In real life situations and ambulatory recordings of biopotential signals, motion artifacts result from relative movement of recording electrodes, cables, and acquisition system with respect to the skin and the environment. The most significant changes during motion are happening on the interface between the skin and the electrodes. These might be due to changes in the charge distribution along the contact surface or skin deformations and hence changes in conduction within the skin. However, different type of movements might induce distinct changes in the measured electrical activity.

A known system that proposes motion artifact removal from ECG signals is described in "*Motion Artifact Removal using Cascade Adaptive Filtering for Ambulatory ECG Monitoring System*", Hyejung Kim et al., IEEE Proceedings of Biomedical Circuits and Systems (BioCAS), 2012.

Another known technique for motion artifact removal from ECG signals is disclosed in "*Implementation of Fuzzy-rule based Activity Classification and Optimized Adaptive Filter-set for Wearable ECG Recording*", Yun-Hong Noh and Do-Un Jeong, International Journal of Multimedia and Ubiquitous Engineering, Vol. 7, No. 4, October 2012. The solution proposes the use of an adaptive filter with an optimal filter coefficient selection to remove motion artifacts. With the data obtained from a three-axis accelerometer, activity status can be classified into different states and optimal filter coefficients can then be selected to minimize the distortion of ECG signal.

U.S. Pat. No. 5,513,649 describes an EEG (electroencephalogram) system that detects brain waves from a subject, and reduces the adverse effect of artifacts due to head, body and eye movements. A head and body movement reference signal can be provided by an accelerometer, motion detector or, alternatively, spatial average of EEG channels. Eye motion sensors are used as a reference for eye movement artifacts.

SUMMARY OF THE INVENTION

The disclosed technology provides new and improved systems and methods for removing motion artifacts from biopotential signals.

Advantageously, according to embodiments of the disclosed technology the disclosed technology adaptively and automatically determines and sets appropriate motion artifact reduction techniques based on the motion type and/or severity affecting the biopotential signal.

According to some exemplary embodiments of the disclosed technology, the disclosed technology is particularly advantageous for wireless, low power data acquisition technology and/or ambulatory biopotential measurement applications.

It is also advantageous that the disclosed technology allows for reliable and high quality biosignal monitoring in ambulatory conditions.

According to some embodiments, it is important to focus on characterizing the effects of human motion on EEG but also other biopotential signals that can be monitored with low-power devices.

According to an exemplary embodiment, there is provided a system for the analysis of biopotential signals, comprising: a motion artifact reduction module configured for reducing or eliminating a motion artifact estimate from a recorded biopotential signal; and a motion classification module configured for determining information about the motion causing the artifacts and communicating said information to the motion artifact reduction module.

According to an exemplary embodiment, the determined information about the motion comprises an indication or classification of type and/or severity of the motion phenomena causing the artifacts in the recorded biopotential signal.

According to an exemplary embodiment, the motion classification module may be configured for determining information about the motion causing the artifacts based on information about one or a combination comprising contact impedance, contact force, motion acceleration, temperature or humidity sensor signals.

According to another exemplary embodiment, the motion classification module may be further configured for determining and communicating setting parameters for artifact removal to the motion artifact reduction module. Said setting parameters may comprise, for example, an artifact removal technique selection indication and/or coefficients related to a given artifact removal technique and/or signal selection indication for a given artifact removal technique.

According to another exemplary embodiment, the motion artifact reduction module may be further configured for applying, configuring and/or optimizing a certain artifact removal technique based on information received from the motion classification module.

In another exemplary embodiment, the motion classification module and the motion artifact reduction module may be configured for performing one or a combination of classification, statistical analysis, spectral analysis, cross-signal analysis, principal component analysis (PCA), independent component analysis (ICA), canonical component analysis (CCA), adaptive filtering (AF), Bayesian filtering (BF) or empirical mode decomposition (EMD) techniques.

According to still another embodiment, the system (100) may further comprise a pre-processing module configured for adapting the received signals in order to be processed by the motion classification module and/or a post-processing module configured for adapting the output signals provided by the motion classification module and/or the motion artifact reduction module.

According to another exemplary embodiment, there is provided a system for the analysis of biopotential signals, comprising: a motion classification module configured for receiving at least one biopotential signal and at least one reference secondary input signal, performing motion artifact classification for determining motion information comprising a type and/or severity indication about motion phenomena causing artifacts in the biopotential signal and communicating said motion information to a motion artifact reduction module; the motion artifact reduction module being configured for performing motion artifact removal from the biopotential signal based on the information received from the motion classification module; and wherein the system is further configured for evaluating the effectiveness of at least one algorithm used for motion artifact removal and generating feedback information between the motion classification module and the motion artifact reduction module for optimizing the performance of the motion artifact classification.

According to an exemplary embodiment, the system is further configured to store and process outputs of a motion classification module and the motion artifact reduction module in different periods of time in order to generate said feedback information for optimizing the performance of the motion artifact classification.

According to another exemplary embodiment, evaluating the effectiveness of at least one algorithm used for motion artifact removal comprises comparing the clean biopotential signal after motion artifact removal with a reference baseline signal of such biopotential signal.

The disclosed technology also relates to an electronic device comprising a system for the analysis of biopotential signals according to any of the embodiments as herein described.

According to another exemplary embodiment there is also provided a method for the analysis of biopotential signals, comprising, in a system: receiving at least one biopotential signal; receiving at least one secondary input signal from a sensor providing direct or indirect information about electrode motion; determining a classification information of the kind of motion causing artifacts in the received biopotential signal; and using that classification information for reducing or eliminating a motion artifact affecting the received biopotential signal.

According to another exemplary embodiment, there is provided a method for the analysis of biopotential signals, comprising, in a system according to an embodiment of the disclosed technology: receiving at least one biopotential signal; receiving at least one secondary input signal; performing motion artifact classification for determining motion information comprising a type and/or severity indication about motion phenomena causing artifacts in the biopotential signal; performing removal of the motion artifact from the biopotential signal based on that motion artifact classification; and evaluating the effectiveness of the removal of the motion artifact from the biopotential signal and generating feedback information for optimizing the performance of the motion artifact classification.

One aspect of the disclosed technology provides for a system for the analysis of biopotential signals. The system includes a motion classification module configured to receive at least one biopotential signal and at least one reference secondary input signal. The motion classification module is further configured to perform motion artifact classification for determining motion meta-information comprising a type and/or severity indication about motion phenomena causing artifacts in the biopotential signal. The motion classification module is further configured to communicate said motion meta-information to a motion artifact reduction module that the system includes. The motion artifact reduction module is configured to perform motion artifact removal from the received biopotential signal based on the information received from the motion classification module. The system is further configured to evaluate the effectiveness of at least one algorithm used for motion artifact removal and the system further configured to generate feedback information between the motion classification module and the motion artifact reduction module for optimizing the performance of the motion artifact classification.

Another aspect of the disclosed technology provides for a method for the analysis of biopotential signals. The method includes receiving at least one biopotential signal. The method includes receiving at least one reference secondary input signal. The method includes performing motion artifact classification for determining motion meta-information comprising a type and/or severity indication about motion phenomena causing motion artifacts in the biopotential signal. The method includes performing removal of the motion artifacts from the biopotential signal based on that motion artifact classification. The method includes evaluating the effectiveness of the removal of the motion artifacts from the biopotential signal. The method includes generating feedback information for optimizing the performance of the motion artifact classification.

Another aspect of the disclosed technology provides for a system for the analysis of biopotential signals. The system includes means for receiving at least one biopotential signal. The system also includes means for receiving at least one reference secondary input signal. The system also includes means for performing motion artifact classification for determining motion meta-information comprising a type and/or severity indication about motion phenomena causing motion artifacts in the biopotential signal. The system also includes means for performing removal of the motion artifacts from the biopotential signal based on that motion artifact classification. The system also includes means for evaluating the effectiveness of the removal of the motion artifacts from the biopotential signal. The system also includes means for generating feedback information for optimizing the performance of the motion artifact classification.

Another aspect of the disclosed technology provides for a non-transitory computer readable medium, comprising computer executable instructions for causing a processor to perform a method for the analysis of biopotential signals. The method includes receiving at least one biopotential signal. The method includes receiving at least one reference secondary input signal. The method includes performing motion artifact classification for determining motion meta-information comprising a type and/or severity indication about motion phenomena causing motion artifacts in the biopotential signal. The method includes performing removal of the motion artifacts from the biopotential signal based on that motion artifact classification. The method includes evaluating the effectiveness of the removal of the motion artifacts from the biopotential signal. The method includes generating feedback information for optimizing the performance of the motion artifact classification.

Certain objects and advantages of various new and inventive aspects have been described above. It is to be understood that not necessarily all such objects or advantages may be achieved in accordance with any particular embodiment of the present invention. Those skilled in the art will recognize that the solution of the present invention may be embodied or carried out in a manner that achieves or optimizes one advantage or group of advantages without necessarily achieving other objects or advantages.

BRIEF DESCRIPTION OF THE DRAWINGS

The above and other aspects of the system and a method according to the disclosed technology will be shown and explained with reference to the non-restrictive example embodiments described hereinafter.

DETAILED DESCRIPTION OF THE INVENTION

Figure 1:
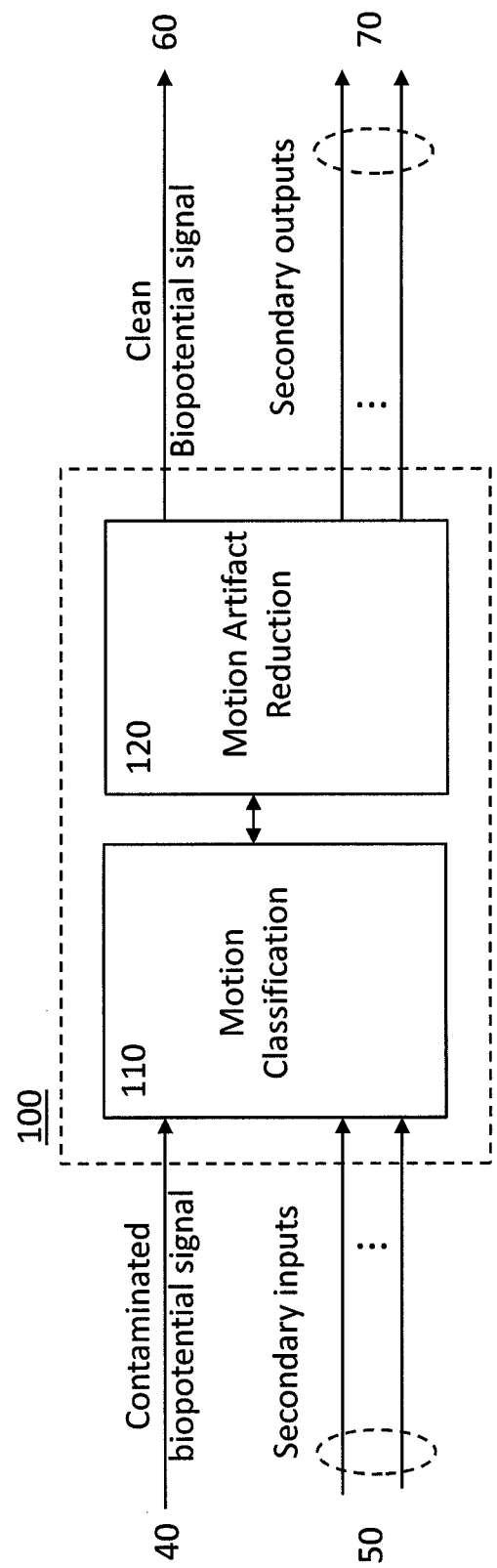
FIG. 1 shows a general block diagram of a system for the analysis of biopotential signals according to a first exemplary embodiment.

In the following, in the description of exemplary embodiments, various features may be grouped together in a single embodiment, figure, or description thereof for the purpose of streamlining the disclosure and aiding in the understanding of one or more of the various inventive aspects. This is however not to be interpreted as the invention requiring more features than the ones expressly recited in the main claim. Furthermore, combinations of features of different embodiments are meant to be within the scope of the invention, as would be clearly understood by those skilled in the art. Additionally, in other instances, well-known methods, structures and techniques have not been shown in detail in order not to obscure an understanding of the description.

Definitions

In order to facilitate an understanding of the systems and methods discussed herein, a number of terms are defined below. The terms defined below, as well as other terms used herein, should be construed to include the provided definitions, the ordinary and customary meaning of the terms, and any other implied meaning for the respective terms. Thus, the definitions below do not limit the meaning of these terms, but only provide exemplary definitions.

The terms "module," "processor module," "microprocessor" and "processor" as used herein are broad terms and are to be given their ordinary and customary meaning to a person of ordinary skill in the art, and furthermore refer without limitation to a computer system, state machine, and the like that performs arithmetic and logic operations using logic circuitry that responds to and processes the basic instructions that drive a computer. These entities may be implemented as single or multiple interconnected modules or processors in hardware, firmware, and/or software. Multiple modules may be combined in a single module or processor.

The term "algorithm" as used herein is a broad term and is to be given its ordinary and customary meaning to a person of ordinary skill in the art, and furthermore refers without limitation to a computational process (associated with computer programming or other written instructions) involved in transforming information from one state to another.

The term "sensor" as used herein is a broad term and is to be given its ordinary and customary meaning to a person of ordinary skill in the art, and furthermore refers without limitation to any device (or portion of a device) that measures a physical quantity and converts it into a signal that can be processed by analog and/or digital circuitry. Thus, the output of a sensor may be an analog and/or digital signal. Examples of sensors include electrocardiograms, electroencephalograms, electromyographs, temperature sensors, altitude sensors, accelerometers, and heart rate sensors.

The terms "sensor data", as used herein is a broad term and is to be given its ordinary and customary meaning to a person of ordinary skill in the art, and furthermore refers without limitation to any data associated with a sensor, such as an EEG, ECG, or EMG. Sensor data includes a raw data stream, or simply data stream, of an analog or digital signal, e.g., directly related to a measured EEG signal or other signal received from another type of sensor, as well as calibrated and/or filtered raw data.

The term "acceleration" as used herein, is a broad term and is used in its ordinary sense, including, but not limited to, the rate of change of velocity with respect to time. This term is broad enough to include deceleration.

The term "deviation," as used herein, is a broad term and is used in its ordinary sense, including, but not limited to, a statistical measure representing the difference between different data sets. The term is broad enough to encompass the deviation represented as a correlation of data.

The terms "statistical parameters" and "statistical," as used herein, are broad terms and are used in their ordinary sense, including, but not limited to, information computed from the values of a sampling of data. For example, noise or variability in data can be statistically measured.

The term "period of time" or "time period," as used herein, is a broad term and is used in its ordinary sense, including, but not limited to, an amount of time including a single point in time and a path (for example, range of time) that extends from a first point in time to a second point in time.

The term "computer," as used herein, is broad term and is used in its ordinary sense, including, but not limited to, machine that can be programmed to manipulate data.

FIG. 1 shows a general block diagram of an exemplary system 100 for the analysis of biopotential signals. The system 100 comprises a motion classification module 110 configured for analyzing the input signals 40, 50, extracting meta-information about the motion, determining the type of motion causing the artifacts and communicating settings for artifact removal to a motion artifact reduction module 120. According to one exemplary embodiment, the motion artifact reduction module 120 is configured for receiving information from the motion classification module 110 and performing artifact removal based on available signal input and information received. According to another exemplary embodiment, the motion artifact reduction module 120 may also provide information or data to the motion classification module 110, for example for updating some parameters.

The system 100 may receive at least one biopotential signal 40 which may be contaminated by a motion artifact and one or more secondary inputs 50 related to the subject or electrode motion and/or direct or indirect artifact distortion causes. The system 100 may provide as output: at least one cleaned biopotential signal 60 which is the result of applying some motion artifact reduction technique(s) to the received contaminated biopotential signal 40 and secondary outputs 70 with motion meta-information about the type and features of the motion detected.

According to an exemplary embodiment, extraction of a clean EEG signal from the contaminated one may be performed in the system 100 based on the meta-information extracted from one or more reference secondary input signals 50, such as, but not limited to, electrode-to-tissue impedance, applied or contact force or acceleration of/on the electrode. The meta-information extracted from those reference secondary inputs 50 may comprise, but is not limited to, signal properties, such as standard deviation, slope and/or higher-order statistics. From such extracted meta-information, certain optimized filtering methods and parameters may be automatically selected. According to an exemplary embodiment, the system 100 is configured for selecting the most appropriate filtering technique for a determined type and severity of motion that affects the biopotential signal and to adjust certain filter or other motion artifact reduction settings to be applied to the contaminated biopotential signal. Such filtering techniques may include, but are not limited to, adaptive filtering, ICA, and/or wavelet decomposition.

Figure 2:
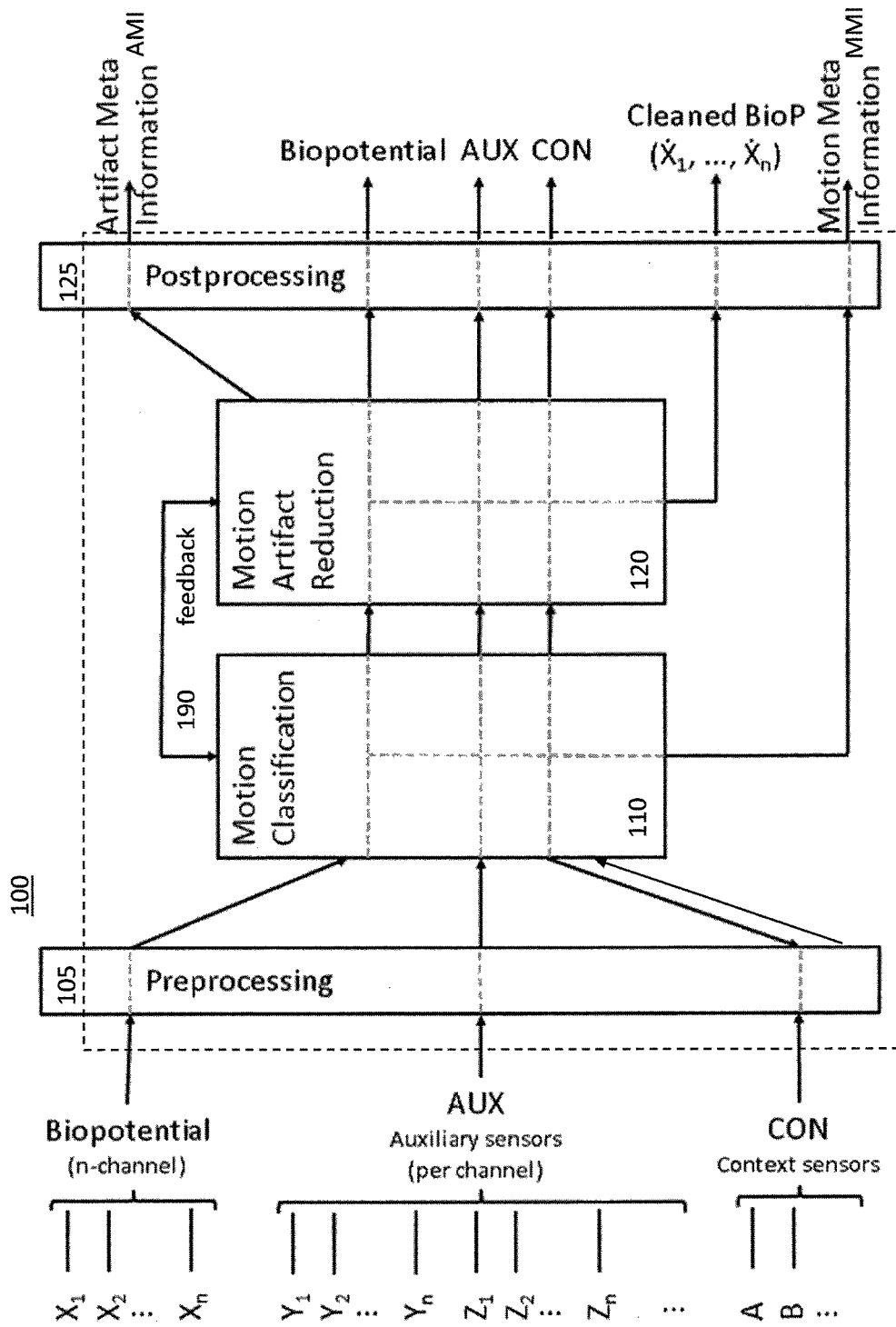
FIG. 2 shows a block diagram of a system for the analysis of biopotential signals according to a second exemplary embodiment.

FIG. 2 shows another block diagram of an exemplary system 100 for the analysis of biopotential signals. The system 100 may comprise a pre-processing module 105 configured for performing basic signal preprocessing required before motion classification and/or artifact handling. The pre-processing module 105 may comprise simple linear filtering (e.g., for removing power line noise), resampling, etc. The system 100 further comprises a motion classification module 110 configured for analyzing the input signals, estimating the kind of motion that causes the artifacts, extracting meta information about the motion, and/or communicating optimized settings for artifact removal to the motion artifact reduction module 120. According to one exemplary embodiment, the motion artifact reduction module 120 is configured for receiving information from the motion classification module 110 and performing artifact reduction based on available signal input. According to another exemplary embodiment, the motion artifact reduction module 120 may also provide input information or data 190 for the motion classification module 110, for example for updating some parameters. After the motion artifact reduction module 120, a post-processing module 125 may be provided for formatting the output information or signals, along with the raw input received by the system. According to an exemplary embodiment, the post-processing module 125 may be configured also for combining the outputs of different artifact removal methods.

The system 100 may receive: a) biopotential input signals X1 to Xn consisting of n biopotential channels/electrodes measuring biopotential of interest at different locations. Biopotential signals may be, but are not limited to, EEG, ECG or EMG signals; b) auxiliary sensor input signals AUX such as, but not limited to, contact impedance, contact force and/or acceleration of the sensors. Said sensors may be, but not necessarily, located at the electrodes; and/or c) contextual sensor input signals CON such as, but not limited to, acceleration, temperature and/or humidity.

The system 100 may provide, as output: a) motion meta information MMI about the type and features of the motion detected. This can be, for example, a type of motion (e.g., walking, running), or the severity of the impact of motion on the biopotential signal of interest; b) artifact meta information AMI about the artifact removal method(s) used, along with the additional information that might be useful; and/or c) cleaned biopotential signals Cleaned BioP which are the result of applying artifact reduction techniques on the biopotential input signals. The cleaned biopotential signals are signals in which the artifact contamination has been totally or partially removed.

Figure 3:
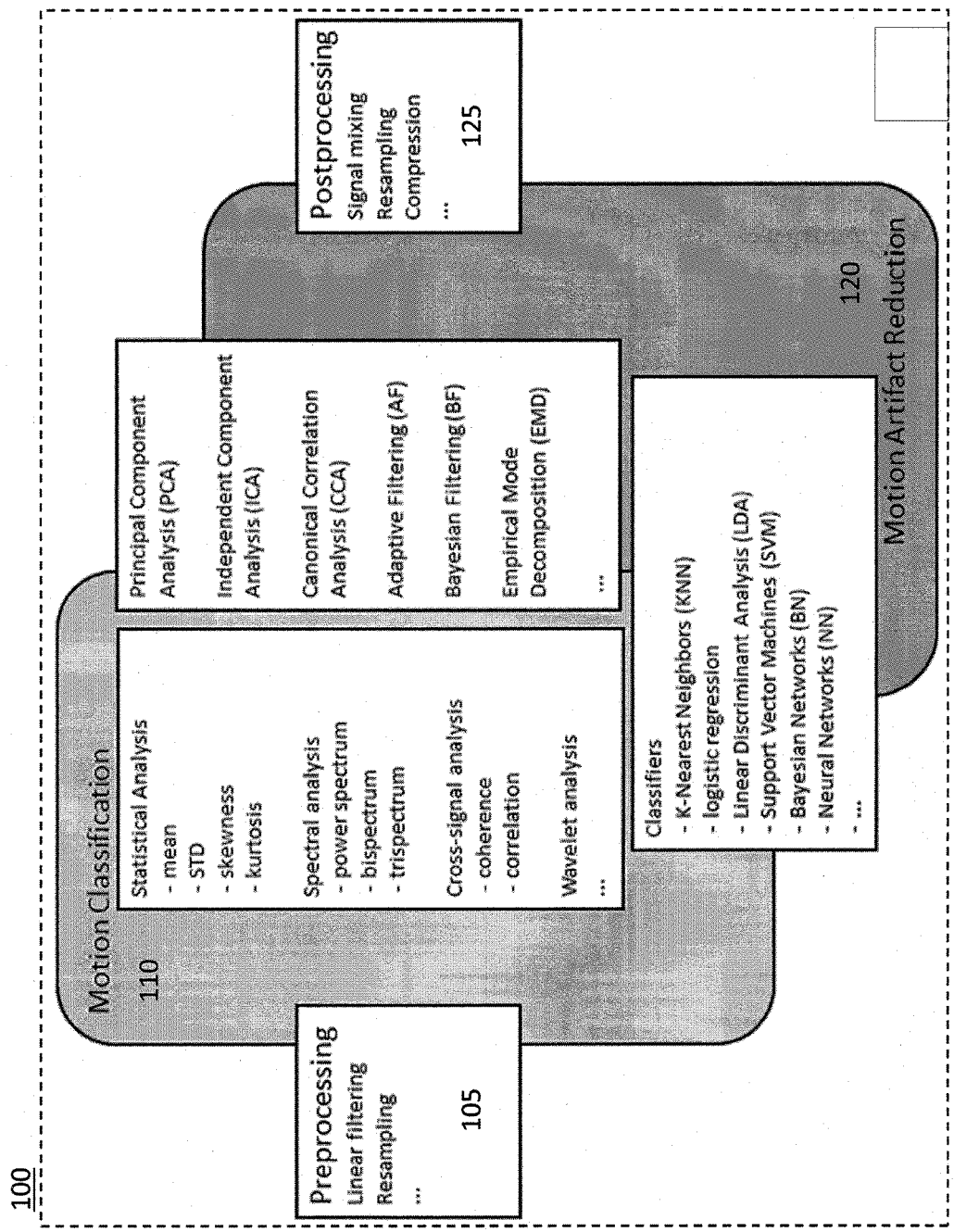
FIG. 3 shows a schematic block diagram of a system for the analysis of biopotential signals according to a third exemplary embodiment.

FIG. 3 shows another schematic block diagram of an exemplary system 100 for the analysis of biopotential signals. According to an exemplary embodiment, the motion classification module 110 and the motion artifact reduction module 120 may share methods and algorithms used for signal analysis and classification.

According to an exemplary embodiment, the motion classification module 110 may be configured for carrying out some classification techniques in combination with statistical analysis, spectral analysis, cross-signal analysis, and/or wavelet analysis methods. A list of such possible methods can be found, for example, in paper "*Introduction to Applied Statistical Signal Analysis*", by Richard Shiavi, Elsevier Inc., 3rd edition, San Diego, 2006, but it may also include higher (than 4) order statistics, and/or non-linear signal analysis methods. According to another exemplary embodiment, the motion classification module 110 may be also configured for performing some artifact handling functions, such as, for example, PCA, ICA and/or CCA. According to another exemplary embodiment the motion classification module 110 may be also configured for carrying out some classification algorithms, such as K-nearest neighbors (KNN), linear discriminant analysis (LDA), support vector machines (SVM), Bayesian networks (BN), and neural networks (NN). A description of such algorithms can be found in the literature and are known for the person skilled in the art.

According to an exemplary embodiment, the motion artifact reduction module 120 may be configured for carrying out procedures such as, for example, PCA, ICA, CCA, AF, BF, and/or EMD. A recent review of such methods is disclosed in paper "*Artifact Removal in Physiological Signals—Practices and Possibilities*", by Kevin T. Sweeney et al., IEEE Transactions on Information Technology in Biomedicine, Vol. 16, Issue 3, pages 488-500, 2012. According to another exemplary embodiment, the motion artifact reduction module 120 may be also configured for performing cross-signal analysis, wavelet analysis, etc., and/or may also perform some of the classification methods.

It shall be understood, for a person skilled in the art, that the above introduced list of methods and techniques, individually or in combinations, is not exhaustive.

Figure 4A:
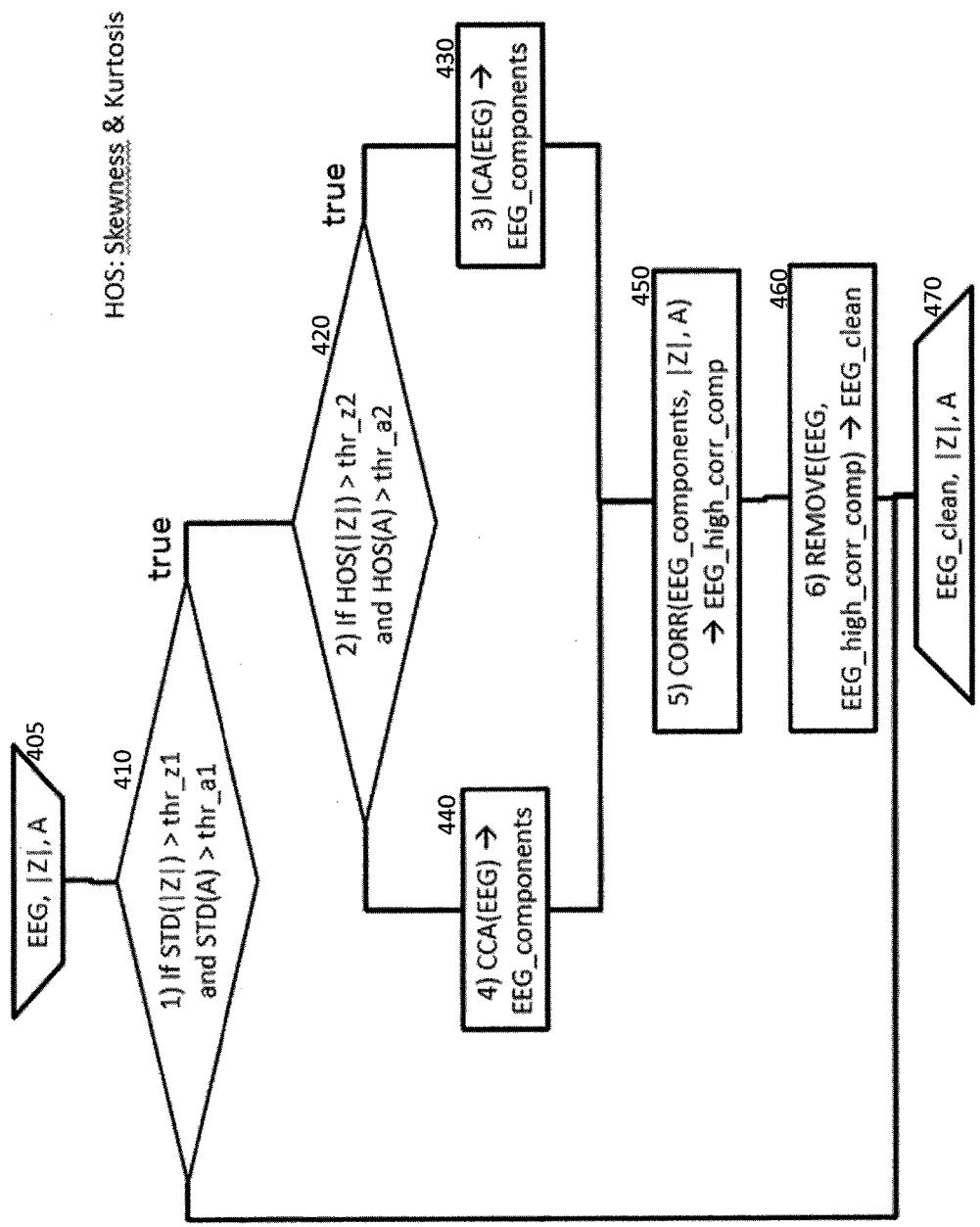
FIG. 4A shows a flow diagram of a method for the analysis of an EEG signal according to a first exemplary embodiment.

FIG. 4A shows a flow diagram of a method for the analysis of an EEG signal according to a first exemplary embodiment. The method is based on the usage of information about electrode-to-skin impedance Z, electrode (3-axis) acceleration motion A, and the EEG as the biopotential signal of interest EEG. According to an exemplary embodiment, the motion classification module 110 may be configured for determining and analyzing the standard deviation, skewness (skew) and kurtosis of the impedance magnitude |Z| and acceleration signals A. Based on the output of the motion classification module 110, the motion artifact reduction module 120 may either perform CCA or ICA techniques.

Figure 4B:
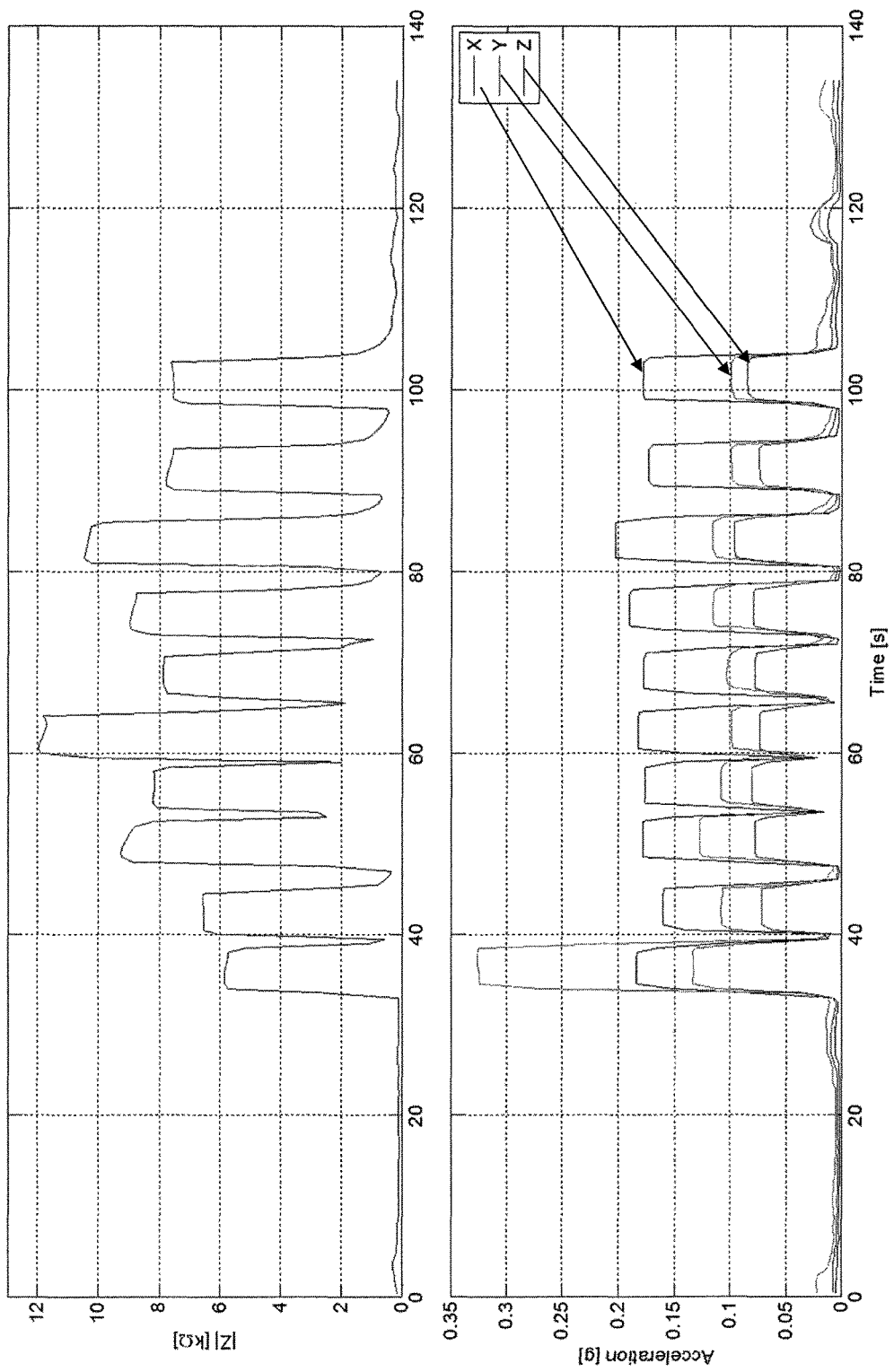
FIG. 4B illustrates an exemplary graph of the standard deviation of measured electrode-to-skin impedance and 3-axis motion acceleration signals during EEG monitoring when applying the method shown in FIG. 4A.

The method may comprise the following steps shown in the flowchart of FIG. 4A, starting in block 405 with an EEG with motion artifacts and ending in a clean EEG in block 470. In step 1 (block 410), if standard deviation of impedance magnitude and (or) acceleration in all (or a subset of) directions is larger than predetermined threshold, then go to step 2 (block 420). Otherwise provide the clean EEG signal (and eventually information about the impedance and acceleration signals). FIG. 4B illustrates, for example, the standard deviation of those signals during an EEG recording that contains artifacts between seconds 35 and 105. According to an exemplary embodiment, the threshold values can be set to 1 kΩ for impedance magnitude and 0.025 g for acceleration.

Figure 4C:
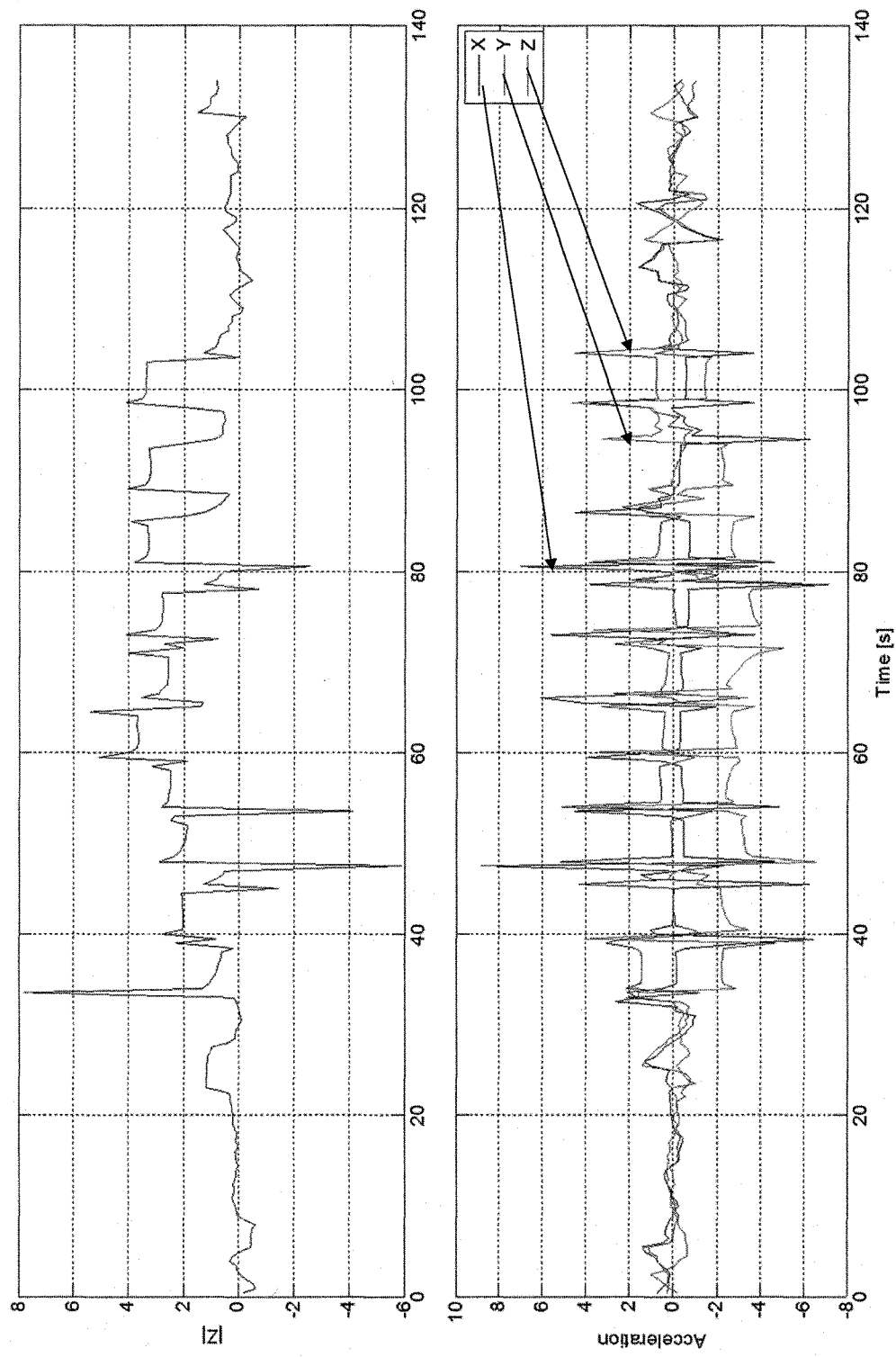
FIG. 4C shows the skewness of the signals shown in FIG. 4B.
Figure 4D:
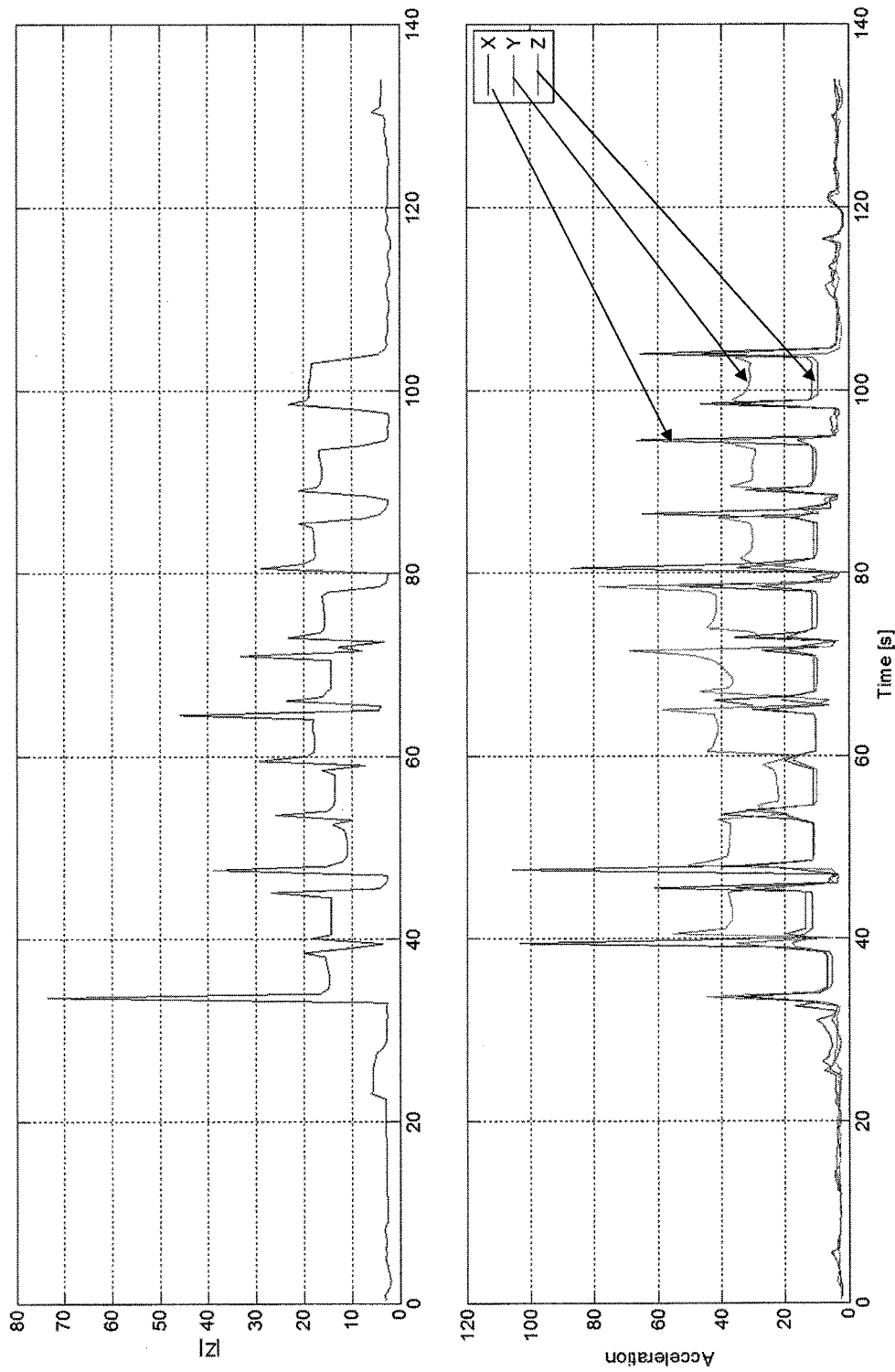
FIG. 4D shows the kurtosis of the signals shown in FIG. 4B.

In step 2 (block 420), if skewness and (or) kurtosis higher order statistics (HOS) of impedance magnitude and (or) acceleration in all (or a subset of) directions is larger than the predefined threshold, then go to step 3 (block 430). Otherwise go to step 4 (block 440). As an example, FIGS. 4C and 4D illustrate, respectively, the skewness and kurtosis of the impedance magnitude and acceleration for the same segment as depicted in FIG. 4B.

Figure 4E:
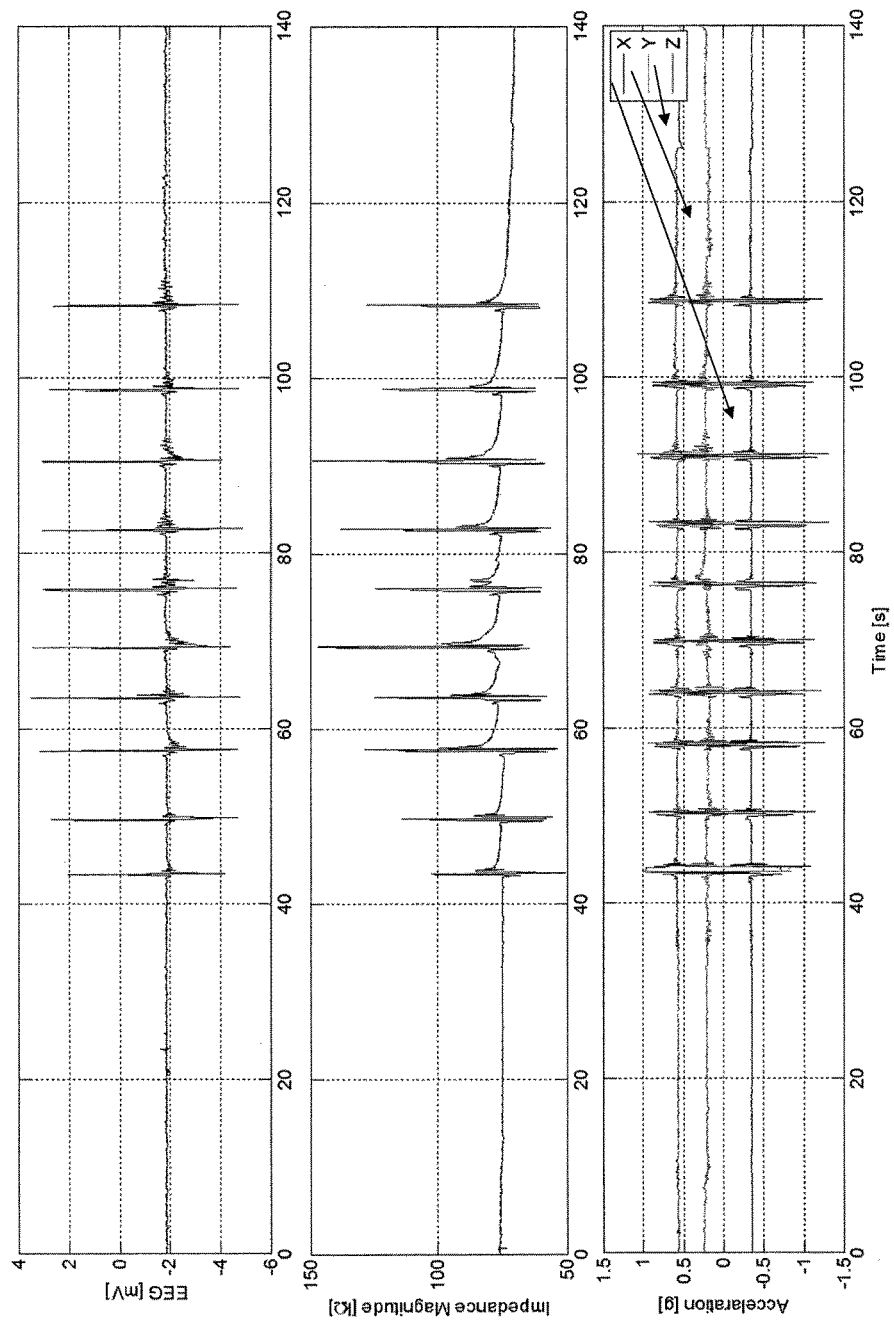
FIG. 4E illustrates an exemplary graph of the magnitude of measured electrode-to-skin impedance and 3-axis motion acceleration signals during EEG analysis when applying a method as shown in FIG. 4A.

In step 3 (block 430), use the ICA method to extract the components from the EEG (and other signals), since ICA uses higher order statistics (e.g., skewness and kurtosis) in the analysis and then go to step 5 (block 450). In step 4 (block 440), use the CCA method to extract the components from the EEG (and other signals), since CCA uses only first and second order statistics (e.g., mean and standard deviation) in the analysis and then go to step 5 (block 450). In step 5 (block 450), correlate the identified components from the EEG signal(s) with the impedance magnitude and acceleration signals, select the component that has the highest correlation and then go to step 6 (block 460). As an example, FIG. 4E illustrates an EEG signal along impedance magnitude and acceleration signals, for the same segment as in FIGS. 4B to 4D. They can be used to select the component in the EEG that represent the artifact and that is extracted using the ICA or CCA method. In step 6 (block 460), remove the identified component from the EEG signal and reconstruct the 'clean EEG' (Cleaned BioP in FIG. 2).

In case the artifact is not identified, the clean EEG will be the same as the input EEG.

Figure 5A:
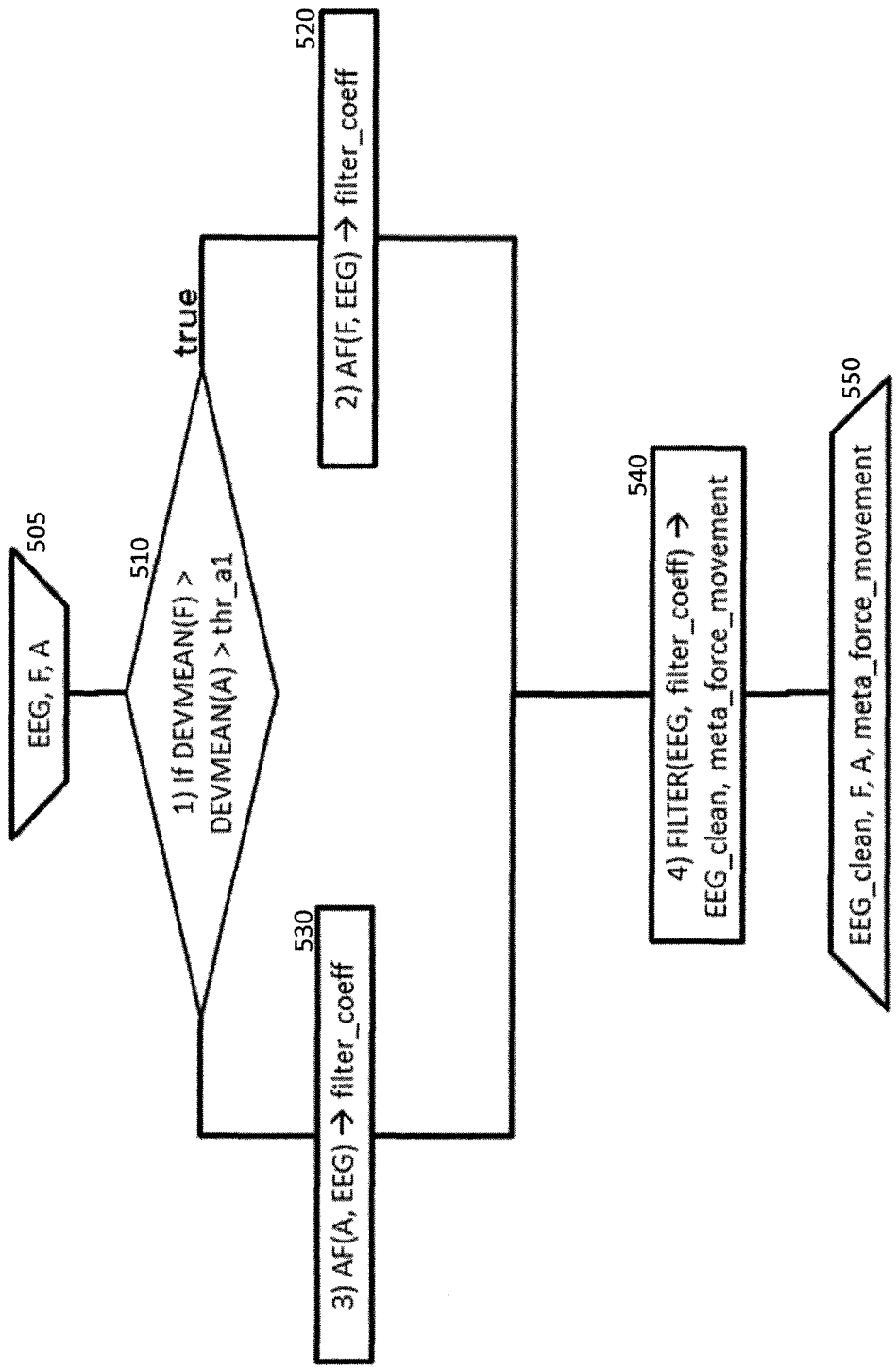
FIG. 5A shows a flow diagram of a method for the analysis of an EEG signal according to a second exemplary embodiment.

FIG. 5A shows a flow diagram of another exemplary method for the analysis of an EEG signal. The method is based on the usage of information about the force applied to an electrode F, electrode (3-axis) acceleration motion A, and the EEG as the biopotential signal of interest EEG. According to an exemplary embodiment, the motion classification module 110 may be configured for determining and analyzing the deviation from the mean and optionally based on a well-tested classifier. Based on the output of the motion classification module 110, the motion artifact reduction module 120 may perform an adaptive filtering method that uses either force or the acceleration signal with the largest deviation from the mean as a reference signal. The selection of the reference signal is also provided by the system as a motion meta Information indicating whether there is a force (pressure) change in one or more electrodes, or there is a head and/or body movement.

Figure 5B:
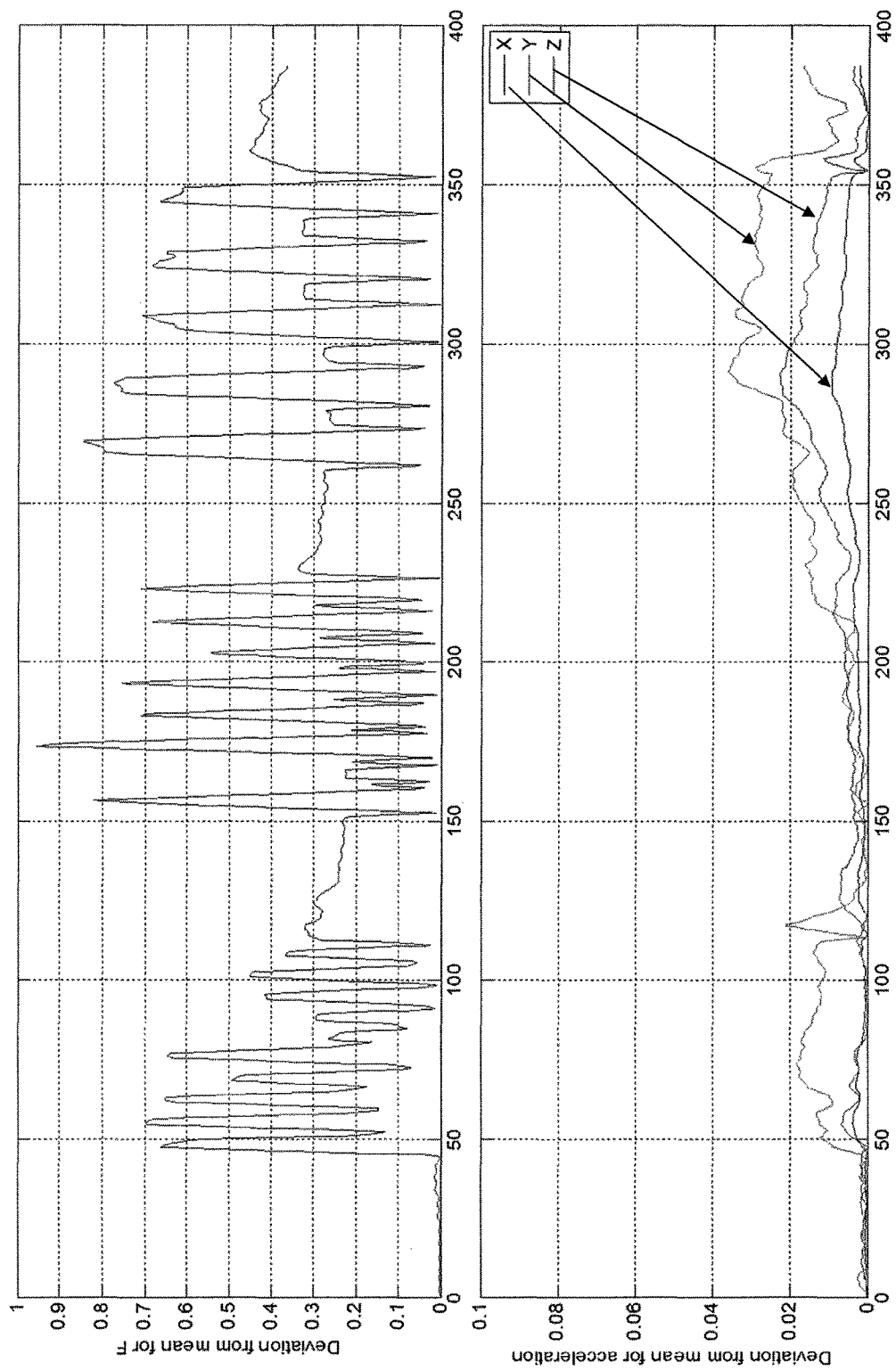
FIG. 5B illustrates an exemplary graph of the deviation from the mean of measured force applied on the electrode and 3-axis motion acceleration signals during EEG monitoring when applying a method as shown in FIG. 5A.

The method may comprise the following steps shown in the flowchart of FIG. 5A, starting in block 505 with an EEG with motion artifacts and ending in a clean EEG in block 550. In step 1 (block 510), if deviation from the mean of the force in all (or a subset of) electrodes is larger than deviation from the mean of acceleration in all (or a subset) of electrodes and in all (or a subset) of directions, then go to step 2 (block 520). Otherwise go to step 3 (block 530). As an example, FIG. 5B illustrates the deviation from the mean during the recording that contains artifacts between second 40 and 360. In the example of the figure, it can be observed that the deviation from the mean for force is much larger than the deviation from the mean for acceleration (in all directions). In case this step is not so obvious, more advanced techniques can be used for making an adequate choice in this step, e.g., using LDA, or KNN classification methods.

Figure 5C:
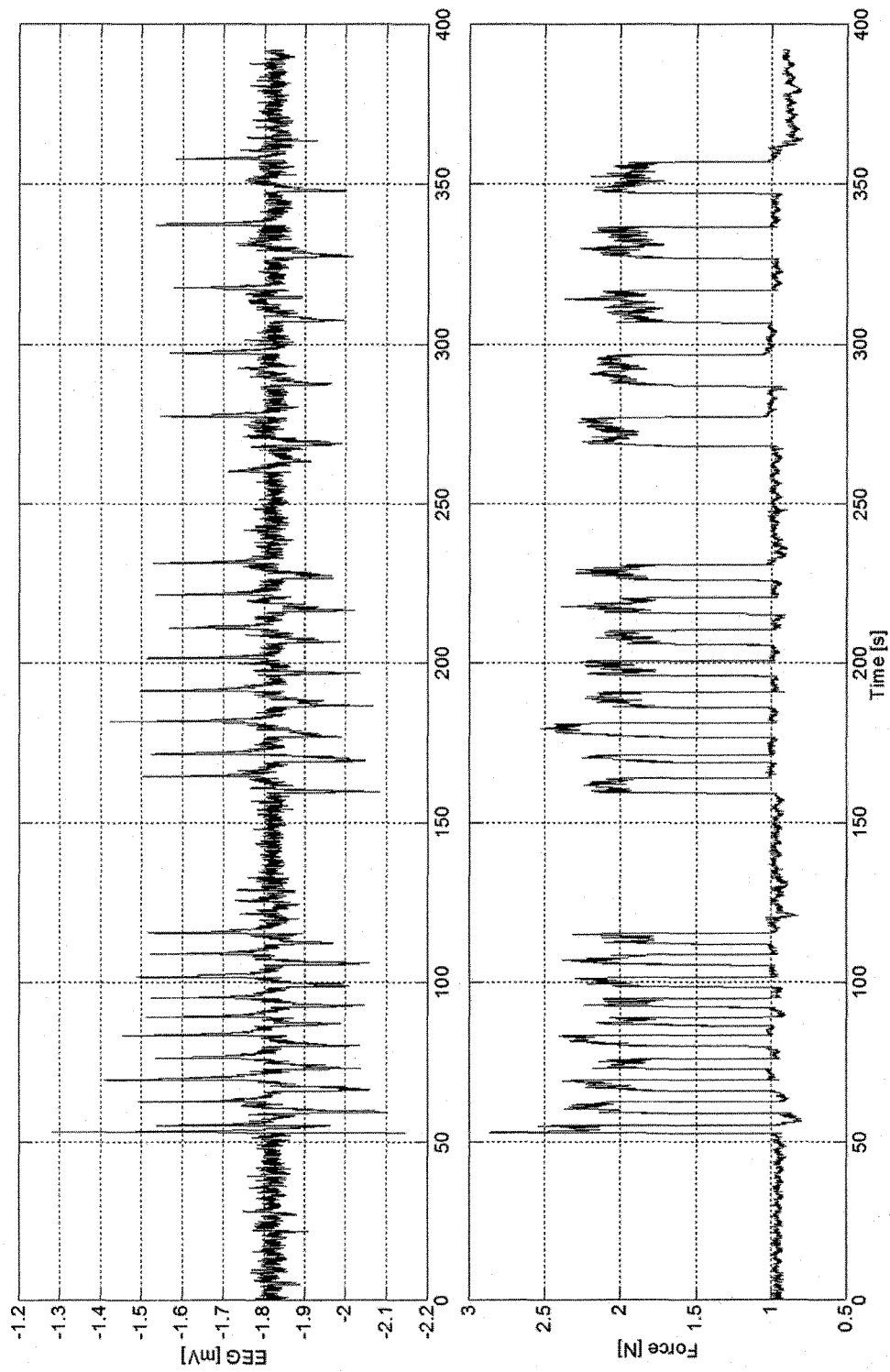
FIG. 5C illustrates an exemplary graph of the magnitude of measured force and an EEG signal during EEG analysis when applying a method shown in FIG. 5A.

In step 2 (block 520), use the AF method with force signal as a reference signal to estimate the filter coefficients and then go to step 4 (block 540). The sample data that can be used in this step is illustrated in FIG. 5C. For a person skilled in the art it is known how AF can be used to remove artifacts from the EEG recording.

In step 3 (block 530), use the AF method with acceleration signal in the direction of the largest deviation from the mean as a reference signal to estimate the filter coefficients and then go to step 4 (block 540).

In step 4 (block 540) use filter coefficient to filter the EEG signal and obtain a clean EEG (Cleaned BioP in FIG. 2) and forward information as the motion meta data that either force was applied on all (or a subset) of electrodes or there is a head/body movement.

Figure 6A:
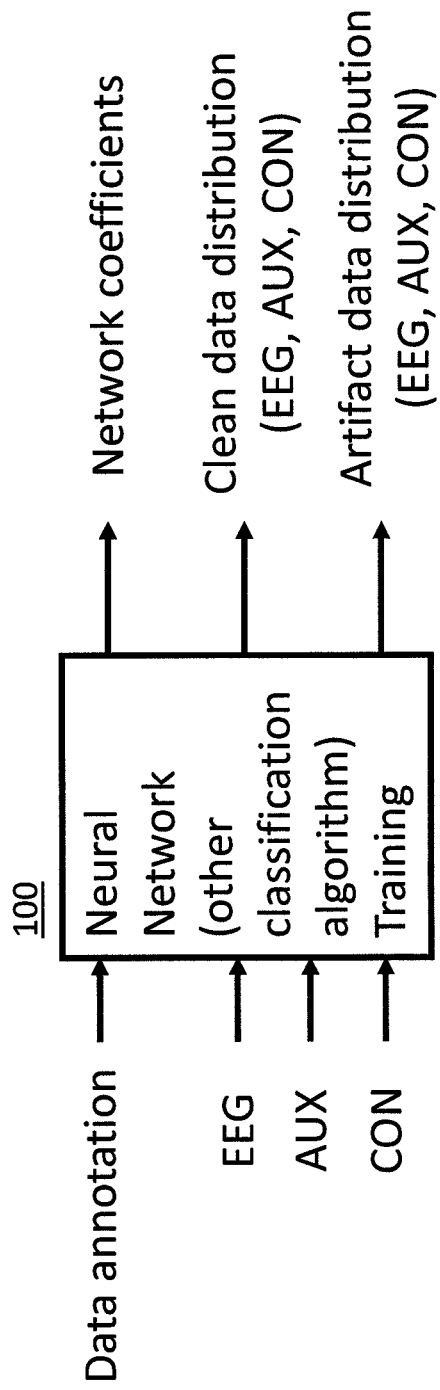
FIG. 6A shows a general block diagram of a system for the analysis of biopotential signals according to a fourth exemplary embodiment.

FIG. 6A shows a general block diagram of another exemplary system for the analysis of biopotential signals.

Figure 6B:
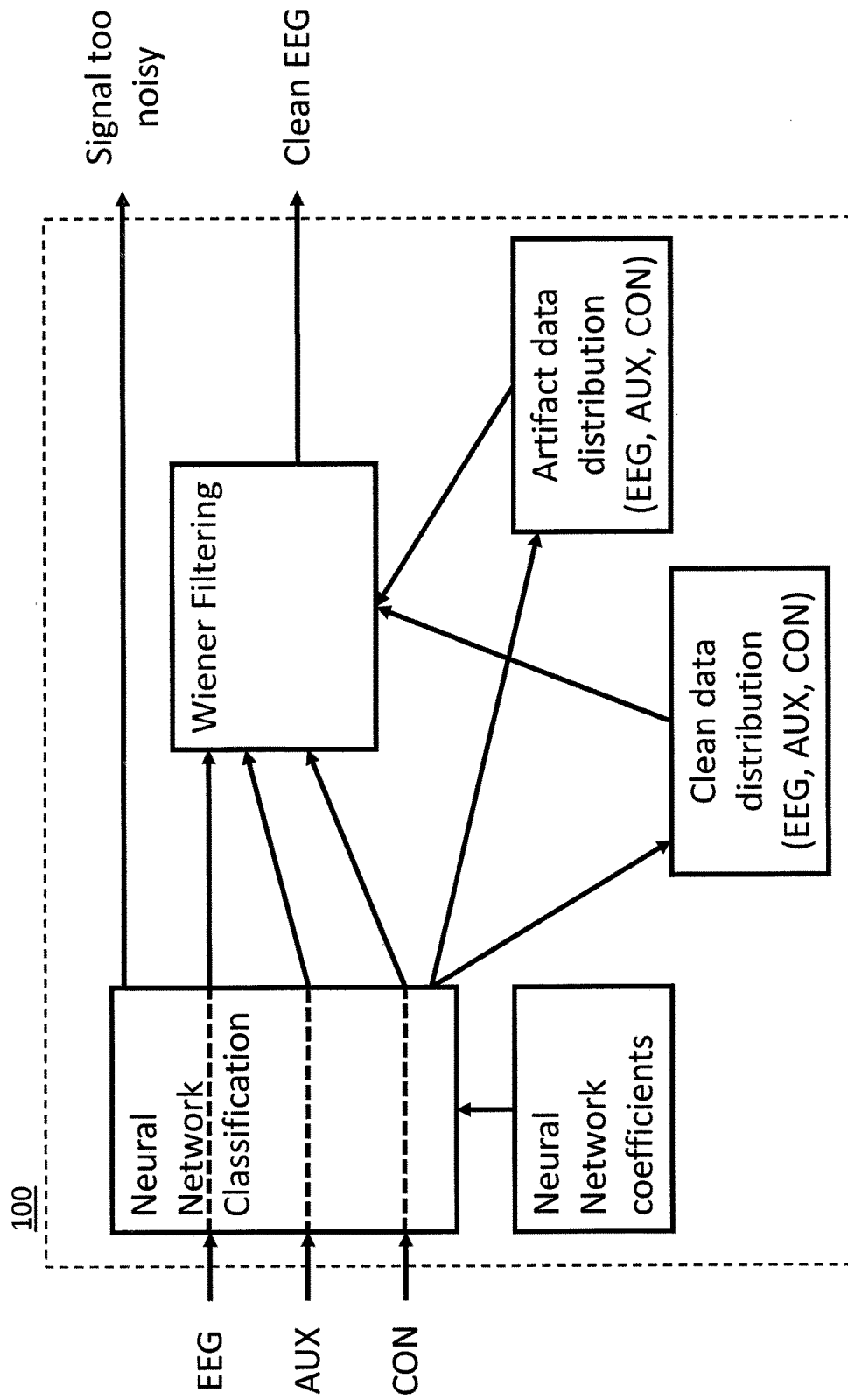
FIG. 6B shows an exemplary block diagram of a system for the analysis of biopotential signals of FIG. 6A.

The system uses all available information that may include biopotential signal(s) (for example, EEG signals), auxiliary signal(s), and contextual information, as an input for the motion classification module 110. The system 100 shows the usage of a neural network (NN), but the embodiment can be based on classifiers other than NN. The usage of such classifier requires training. Training should be performed on the data set that has sufficient samples of the signals obtained during artifact and non-artifact (clean) segments, such that these segments are labeled as e.g., moderate artifact segments, severe artifact segments, and clean segments. Another more detailed exemplary embodiment of the system is illustrated in FIG. 6B. The output of motion classification module 110 during training are the coefficients that will be used for real time operation of the NN as well as data statistics, such as probability density function of different input signals for artifact and clean data segments.

According to another exemplary embodiment, in real-time operation, the motion classification module 110 uses coefficients which are the output of the training stage and the motion artifact reduction module 120 uses data distribution information obtained in the training stage.

Figure 6C:
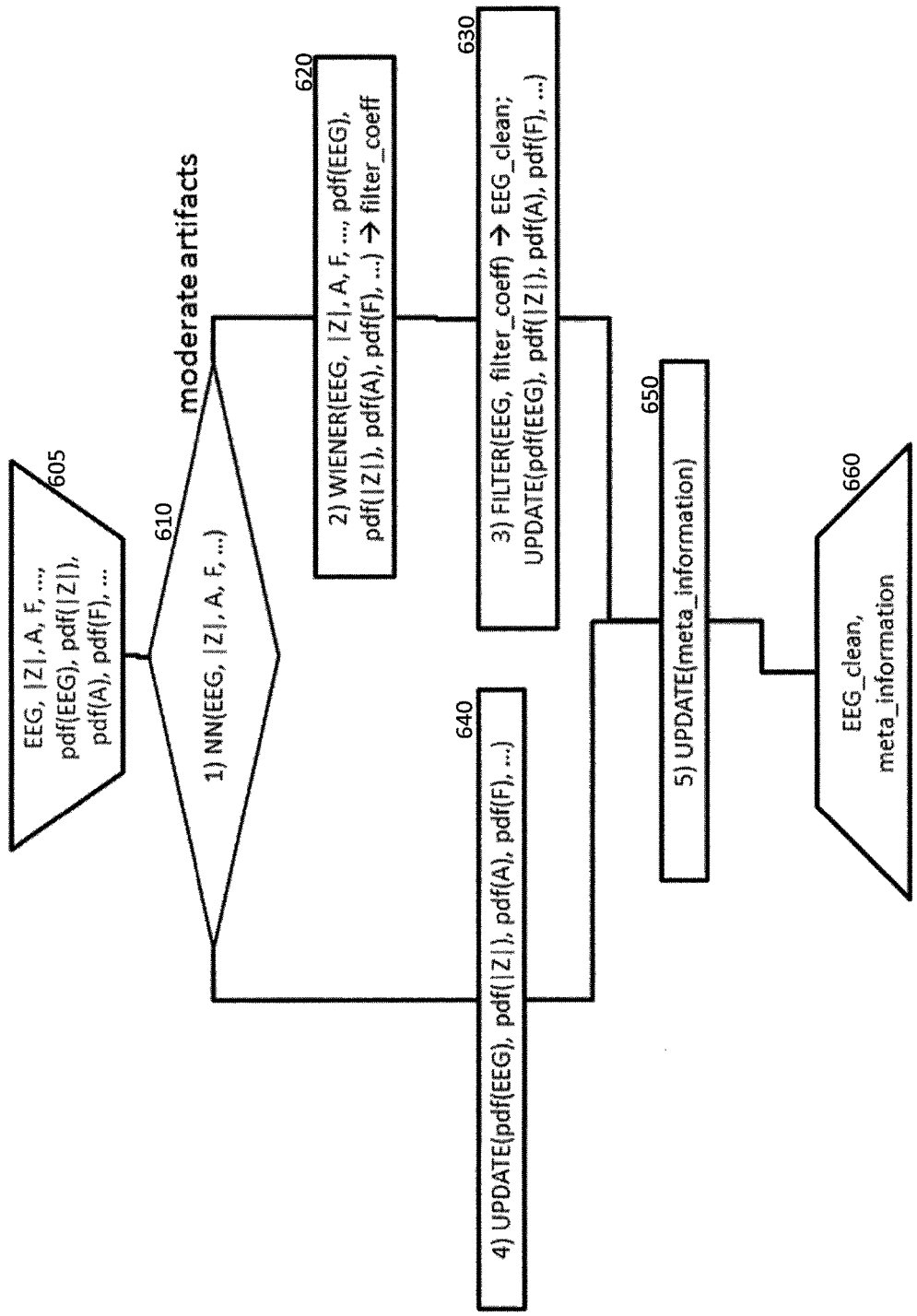
FIG. 6C shows a flow diagram of a method for the analysis of an EEG signal according to a third exemplary embodiment.

FIG. 6C shows a flow diagram of another exemplary method for the analysis of an EEG signal. The method may comprise the following steps shown in the flowchart of FIG. 6C, starting in block 605 with an EEG with motion artifacts and ending in a clean EEG in block 660. In step 1 (block 610), use the Neural Network to classify the input signal(s) (EEG, |Z|, A, F, pdf(EEG), pdf(|Z|), pdf(A), pdf(F)) and in case it is classified as segment with moderate artifacts then go to step 2 (block 620). Otherwise go to step 4 (block 630). The NN is used to distinguish between segments that do not require artifact removal, ones that require, and ones that are too noisy for the artifact removal technique to be effective.

In step 2 (block 620), the information about the data distribution of the clean and contaminated segments (e.g., probability density function) is used as an input for Wiener filtering (or other filtering method that uses information about data distribution pdf(EEG), pdf(|Z|), pdf(A), pdf(F)), resulting in the Wiener filter coefficients (as can be seen in FIG. 6B). After obtaining the coefficients go to step 3 (block 630).

In step 3 (block 630), use a Wiener filtering method and obtain a clean EEG (Cleaned BioP in FIG. 2) based on all available input signals, update the artifact data distribution information pdf(EEG), pdf(|Z|), pdf(A), pdf(F), and go to step 5 (block 650).

In step 4 (block 640), if the NN classifies the segment as a clean data segment, then update the clean data distribution information pdf(EEG), pdf(|Z|), pdf(A), pdf(F) and go to step 5 (block 650).

In step 5 (block 650), output motion meta information based on the output of the classification step, i.e., whether it is a segment with no artifacts, segment with too many artifacts, or a segment where artifact reduction is applied.

It is understood that all the above described embodiments may be implemented by hardware and/or software means, for example, in a microprocessor or microcomputer environment.

Figure 7A:
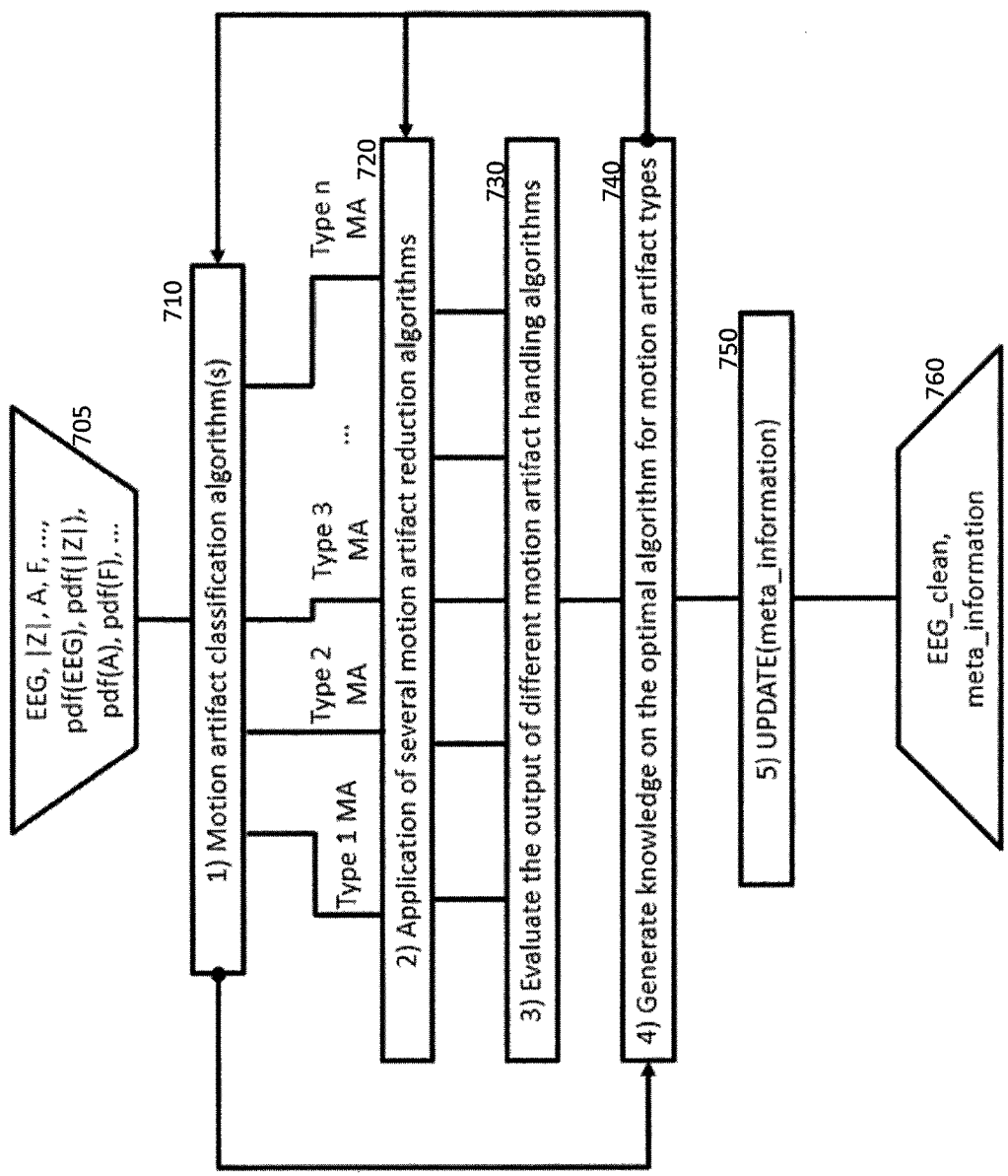
FIG. 7A shows a flow diagram of a method for the analysis of an EEG signal according to a fourth exemplary embodiment.

FIG. 7A shows a flow diagram of a method for the analysis of an EEG signal according to a fourth exemplary embodiment. The method uses all available information that may include biopotential signal(s) (for example, EEG signals), auxiliary signal(s), and contextual information, as an input (EEG, |Z|, A, F, pdf(EEG), pdf(|Z|), pdf(A), pdf(F)) for the motion classification module 110. The motion classification module 110 may use a motion classification approach, but not limited to, as implemented in the exemplary embodiments of FIGS. 4A, 5A and 6A. The output of the motion classification module 110 is then assigned to a segment (i.e., epoch) of biopotential data, denoting what type of motion artifact (MA) is present in the signal Type 1 MA to Type n MA. Several motion artifact reduction algorithms may be available and applied in the motion artifact reduction module 120 and the output of this motion artifact removal algorithms is then evaluated with respect to the expected signal properties and the estimated effectiveness of each of the algorithms is used to build the knowledge on how to optimize motion classification as well as motion artifact reduction.

The method may comprise the following steps shown in the flowchart of FIG. 7A, starting in block 705 with an EEG with motion artifacts and ending in a clean EEG in block 760. In step 1 (block 710), use one or a combination of motion classification algorithms to determine one or more types of motion artifact Type 1 MA to Type n MA. The algorithm(s) used may be pre-defined but may also be based on a built knowledge about the effectiveness of the algorithms for motion artifact handling performed in step 3 and accumulated in step 4. The input signals used in the classification may be predefined but may also be based on the evaluation performed in steps 3 and 4. The knowledge on the optimal algorithm for motion artifact types extracted in step 4 may be used for, but not limited to: adjusting the parameters of the motion artifact classification algorithms (e.g., the thresholds used, the size of the neural network, etc.) to achieve better classification; and/or selecting which algorithm to use (including the selection of parameters for that motion artifact reduction algorithm) to achieve better classification. In step 2 (block 720) several implementations of motion artifact reduction algorithms (and/or their combinations) are applied to the input signals. The algorithm(s) used can be pre-defined but can also be based on a built knowledge about the effectiveness of the algorithms for motion artifact handling performed in step 3 (block 730) and accumulated in step 4 (block 740). The input signals used in the classification can be predefined but may also be based on the evaluation performed in steps 3 and 4 (blocks 730 and 740). The result is a clean EEG (Cleaned BioP in FIG. 2) based on all (or a subset) of available input signals. The knowledge on the optimal algorithm for motion artifact types extracted in step 4 (block 740) can be used for, but not limited to: adjusting the parameters of the motion artifact reduction algorithms (e.g., the number of filter coefficients for adaptive filtering, type of the wavelets used for wavelet transform, etc.) to achieve better motion artifact reduction; and/or selecting which algorithm to use for a specific motion artifact type (including the selection of parameters for that motion artifact reduction algorithm) to achieve better motion artifact reduction; and/or selecting the optimal combination of algorithms to be used (e.g., adaptive filtering and discrete wavelet transform, Wiener filtering and ICA, etc.) to achieve better motion artifact reduction.

Figure 7B:
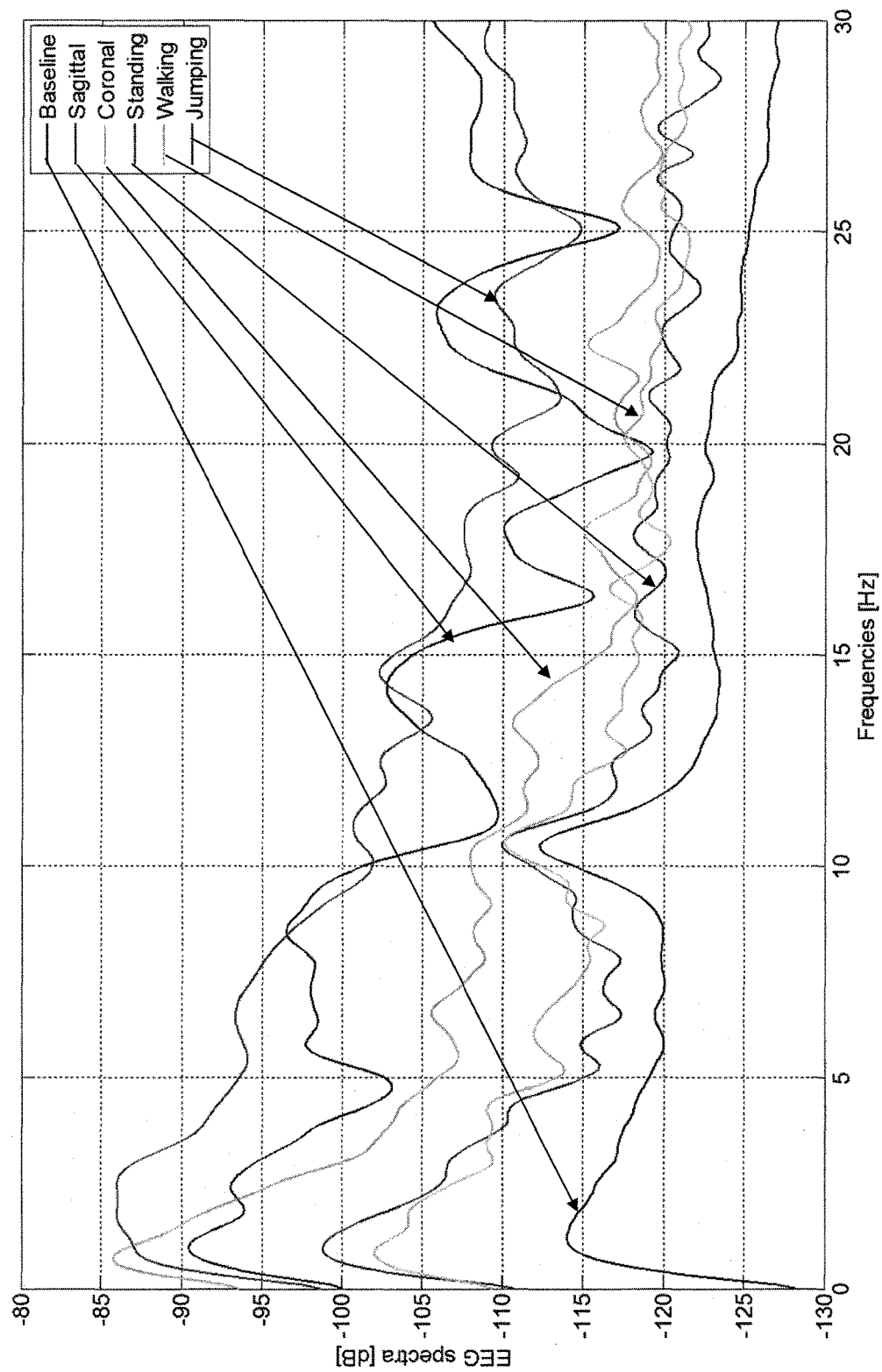
FIG. 7B illustrates an exemplary graph of EEG spectral contents for a baseline EEG and the EEG obtained after application of different types of motion artifact removal during EEG analysis when applying a method as shown in FIG. 7A.
Figure 7C:
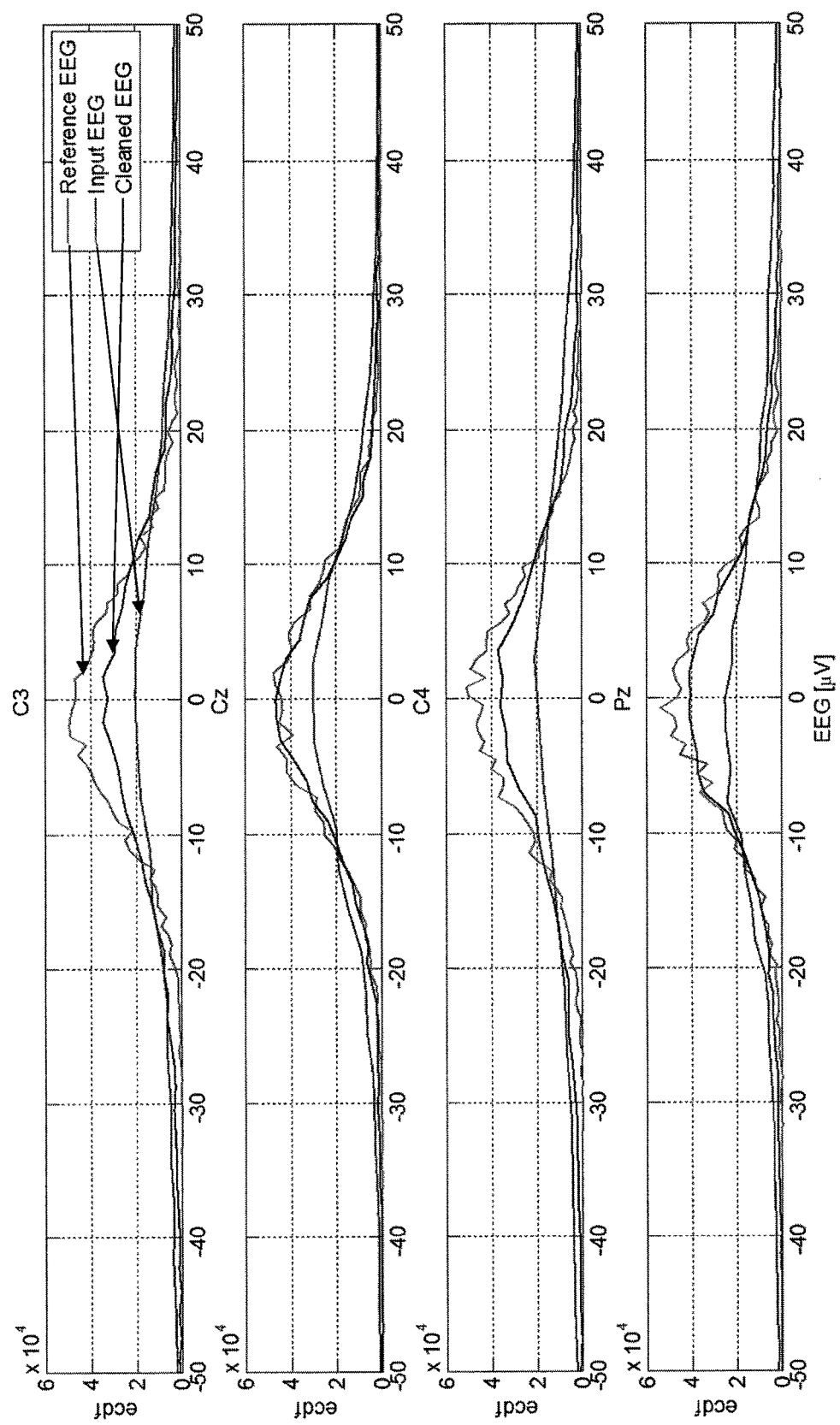
FIG. 7C illustrates an exemplary graph of a distribution of the data points for a reference, input and cleaned EEG signal during EEG analysis when applying a method as shown in FIG. 7A.

In step 3 (block 730) an evaluation of the motion artifact handling algorithm may be done based on comparing the obtained clean EEG signal and the expected signal. In case of an EEG this may be done, for example, by comparing the spectral content of the baseline EEG (without artifact contamination) and the one(s) obtained after application of the artifact removal algorithm(s) (e.g., sagittal, coronal, standing, walking, jumping). Such signals are illustrated in FIG. 7B. Another option for evaluating would be to look at the distribution of the data points between the baseline and the artifact-contaminated signal. Such signals, for an EEG biopotential signal, are illustrated in FIG. 7C. Similarly, in case of an ECG biopotential signal, the obtained clean ECG signal can be compared with a template ECG signal or a baseline one. Other evaluation metrics (or a combination of those) may be used in a similar way.

In step 4 (block 740), based on the evaluation of a) the output of one or more motion artifact reduction algorithm(s) from the motion artifact reduction module 120, b) the output of one or more motion artifact classification algorithm(s) from the motion classification module 110, and, when available, c) previous outputs of these modules on the data segments already processed, feedback information is generated to optimize the performance of the motion artifact classification described in step 1, and motion artifact reduction described in step 2.

In step 5 (block 750), the method may output motion meta-information MMI based on the output of the classification step (step 1), i.e., whether it is a segment with no artifacts, a segment with too much artifacts, or a segment where artifact reduction is applied, which classification algorithm(s) is(are) used and what parameters. Also the information from step 4 is used, describing the optimal setup for motion artifact reduction approach for a certain type of motion artifact.

Further advantageous embodiments and background information of the disclosed technology will be described below. For example, according to an exemplary embodiment of the disclosed technology, extraction of a clean biopotential signal from the contaminated one is performed in two stages. Based on the meta information extracted from one or more reference signals (such as electrode to tissue impedance, force on the electrode or acceleration of the electrode) the proper filtering method and parameters are automatically selected. This is performed by a 'motion classifier' (using signal properties, such as standard deviation, slope, and higher-order statistics) which performs the selection of the filtering technique. Hence, the motion classifier will be used to select the most appropriate filtering technique for the type and severity of motion at hand and to adjust filter settings. Filtering techniques can include adaptive filtering, ICA, wavelet decomposition, etc.

Data supporting the disclosed technology is at least based on the experiment performed with a number of participants where EEG, force, impedance and acceleration were continuously monitored while applying force on dry EEG electrode or performing various movements. The Table given below illustrates the changes that are observed in each of the signals.

jumping). There is a difference between the values of EEG, impedance, force and acceleration across different conditions.

Different conditions also result in different correlation between the signals in question. For example, large correlation coefficient values between the EEG and impedance can be observed for short-term large amplitude changes due to external force (impact force). The correlation of segments containing large changes in force or large changes in acceleration can be characterized. High correlation can be observed (to a lesser degree) for head movements (sagittal and coronal), stand up/sit down movements, force application and release in case of continuous force application, and particularly in the correlation values for jumping segments. Similar outcomes can be observed when looking into correlation of EEG with other signals.

Such results demonstrate that the system can extract information on the type and dynamics of motion based on the signal properties. According to an exemplary embodiment of the disclosed technology, such information may be used in the motion classifier module to select which filtering to apply, what parameters to use in the filtering, as well as which signals to use for removing artifacts. Numerous methods exist in the literature that can be used for artifacts removal that can be part of the system, namely, adaptive filtering, blind source separation methods, wavelet transform, etc. Furthermore, the motion classifier can select a number of them to be applied in sequence or in parallel to have more efficient artifact removal.

Figure 8:
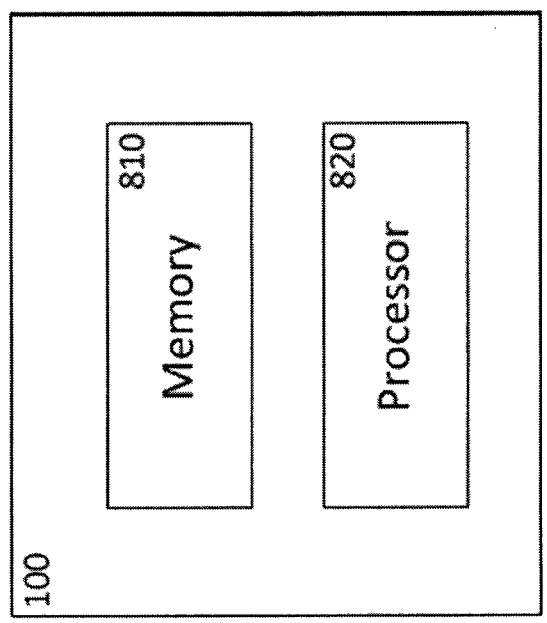
FIG. 8 shows a functional block diagram of an exemplary device for the analysis of biopotential signals.

FIG. 8 shows an exemplary functional block diagram of a device 100 that may be employed when analyzing biopotential signals. Device 100 is an example of a device that may be configured to implement the various methods described herein. The processor 820 may perform the functions associated with the motion classification module 110, the motion artifact reduction module 120, the pre-processing module 105, and the post-processing module 125.

The device 100 may include a processor 820 which controls operation of the device 100. The processor 820 may also be referred to as a central processing unit (CPU). Memory 810, which may include both read-only memory (ROM) and random access memory (RAM), may provide instructions and data to the processor 820. A portion of the memory 810 may also include non-volatile random access memory (NVRAM). The processor 820 typically performs logical and arithmetic operations based on program instruc-

|  |  | Con | Rep | Imp | Nod | Til | Sta | Wal | Jum |
|---|---|---|---|---|---|---|---|---|---|
| EEG(mV) | mean | −1.7 ± 0.17 | −1.7 ± 0.09 | −1.7 ± 0.20 | −0.17 ± 0.22 | −1.7 ± 0.23 | −1.7 ± 0.28 | −1.6 ± 0.29 | −1.4 ± 0.61 |
|  | max-min | 3.1 ± 2.41 | 3.0 ± 3.39 | 4.2 ± 1.91 | 2.6 ± 1.25 | 3.8 ± 2.99 | 3.3 ± 2.93 | 11.8 ± 4.77 | 11.9 ± 3.88 |
|  | stdev | 0.1 ± 0.06 | 0.1 ± 0.11 | 0.2 ± 0.15 | 0.1 ± 0.11 | 0.2 ± 0.11 | 1.5 ± 0.13 | 1.0 ± 0.67 | 1.0 ± 0.85 |
| Imp(kΩ) | mean | 39 ± 21 | 35 ± 12 | 41 ± 20 | 57 ± 23 | 53 ± 24 | 52 ± 25 | 56 ± 27 | 59 ± 20 |
|  | max-min | 32 ± 21 | 23 ± 24 | 35 ± 21 | 36 ± 33 | 28 ± 42 | 14 ± 12 | 36 ± 27 | 94 ± 26 |
|  | stdev | 8.7 ± 6.5 | 5.1 ± 3.5 | 5.9 ± 5.6 | 7.5 ± 6.8 | 3.9 ± 5.1 | 1.5 ± 1 | 5.3 ± 5.2 | 7.4 ± 2.5 |
| For(N) | mean | 1.5 ± 0.28 | 1.2 ± 0.25 | 1.0 ± 0.39 | 0.8 ± 0.29 | 0.9 ± 0.26 | 0.8 ± 0.52 | 0.9 ± 0.48 | 0.9 ± 0.53 |
|  | max-min | 4.5 ± 0.73 | 3.2 ± 0.89 | 4.0 ± 1.03 | 1.1 ± 0.49 | 1.1 ± 0.38 | 1.0 ± 0.31 | 1.5 ± 0.55 | 3.1 ± 1.18 |
|  | stdev | 1.0 ± 0.19 | 0.7 ± 0.18 | 0.3 ± 0.11 | 0.3 ± 0.16 | 0.2 ± 0.06 | 0.1 ± 0.03 | 1.6 ± 0.08 | 0.2 ± 0.06 |
| Acc(g) | mean | 0.7 ± 0.06 | 0.7 ± 0.05 | 0.7 ± 0.06 | 0.7 ± 0.05 | 0.7 ± 0.07 | 0.7 ± 0.05 | 0.7 ± 0.05 | 0.7 ± 0.05 |
|  | max-min | 0.2 ± 0.07 | 0.16 ± 0.2 | 0.3 ± 0.18 | 0.4 ± 0.12 | 0.6 ± 0.08 | 0.5 ± 0.11 | 0.6 ± 0.17 | 1.2 ± 0.33 |
|  | stdev | 0.0 ± 0.00 | 0.0 ± 0.00 | 0.0 ± 0.00 | 0.1 ± 0.02 | 0.1 ± 0.01 | 0.0 ± 0.01 | 0.0 ± 0.01 | 0.1 ± 0.02 |

The columns represent different force applications (continuous, repetitive, impact) or different movements (head nodding, head tilting, standing up/sitting down, walking and tions stored within the memory 810. The instructions in the memory 810 may be executable to implement the methods described herein.

The processor 820 may comprise or be a component of a processing system implemented with one or more processors. The one or more processors may be implemented with any combination of general-purpose microprocessors, microcontrollers, digital signal processors (DSPs), field programmable gate array (FPGAs), programmable logic devices (PLDs), controllers, state machines, gated logic, discrete hardware components, dedicated hardware finite state machines, or any other suitable entities that can perform calculations or other manipulations of information.

The processing system may also include machine-readable media for storing software. Software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the one or more processors, cause the processing system to perform the various functions described herein.

Figure 9:
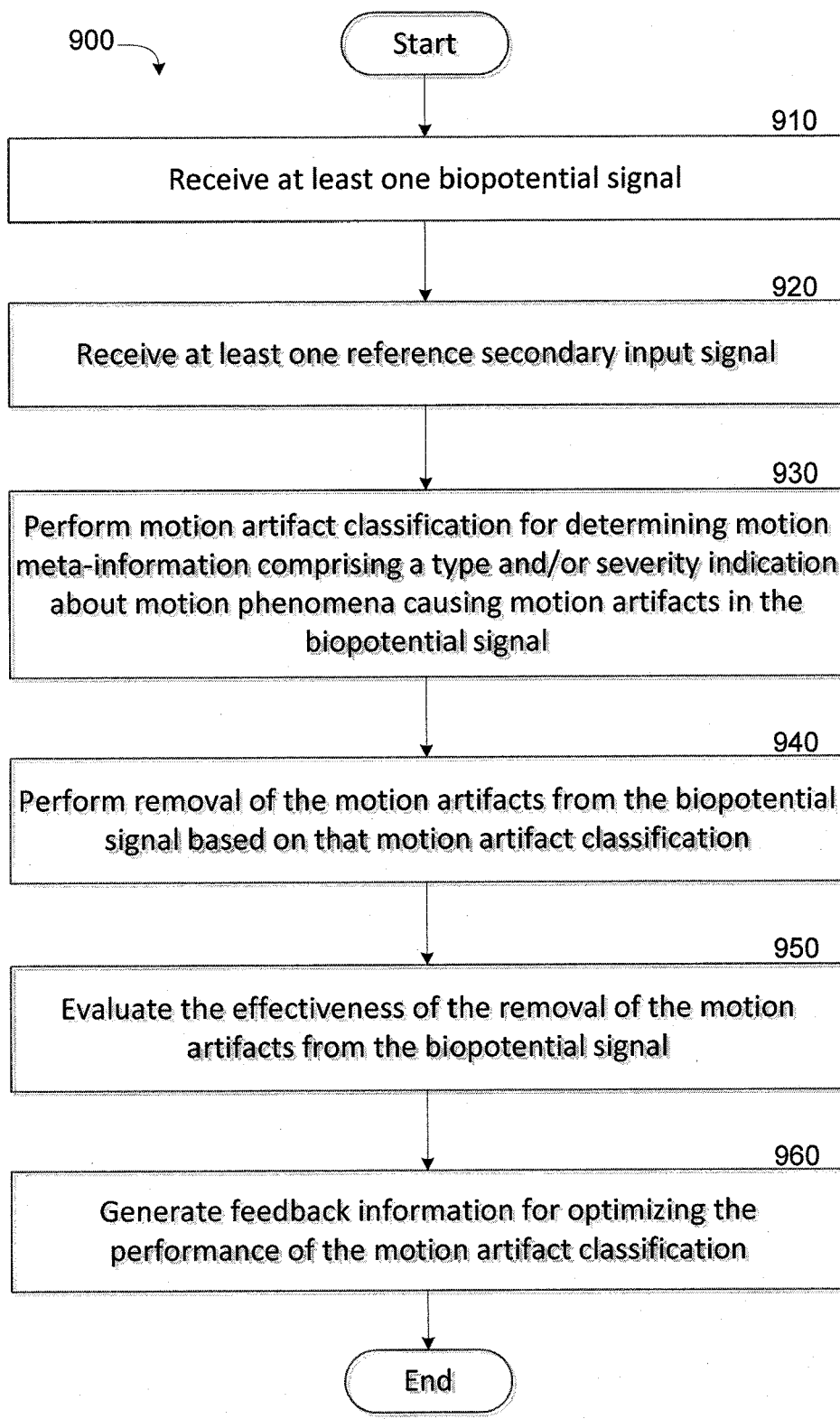
FIG. 9 is a flow chart illustrating a method of analyzing biopotential signals.

FIG. 9 is a flow chart illustrating a method of analyzing biopotential signals using the device shown in FIG. 1, FIG. 2, FIG. 3, and/or FIG. 8. Block 910 of the method receives at least one biopotential signal. Block 920 of the method receives at least one reference secondary input signal. Block 930 of the method performs motion artifact classification for determining motion meta-information comprising a type and/or severity indication about motion phenomena causing motion artifacts in the biopotential signal. Block 940 of the method performs removal of the motion artifacts from the biopotential signal based on that motion artifact classification. Block 950 of the method evaluates the effectiveness of the removal of the motion artifacts from the biopotential signal. Block 960 of the method generates feedback information for optimizing the performance of the motion artifact classification.

Embodiments of the present disclosure are described above and below with reference to flowchart illustrations of methods, apparatus, and computer program products. It will be understood that each block of the flowchart illustrations, and combinations of blocks in the flowchart illustrations, can be implemented by execution of computer program instructions. These computer program instructions may be loaded onto a computer or other programmable data processing apparatus (such as a controller, microcontroller, microprocessor or the like) in a sensor electronics system to produce a machine, such that the instructions which execute on the computer or other programmable data processing apparatus create instructions for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks presented herein.

It should be appreciated that all methods and processes disclosed herein may be used in any biopotential monitoring system. It should further be appreciated that the implementation and/or execution of all methods and processes may be performed by any suitable devices or systems, whether local or remote. Further, any combination of devices or systems may be used to implement the present methods and processes.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range, is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A system for analysis of biopotential signals, comprising:

a motion classification module; and a motion artifact reduction module, wherein the motion classification module is configured to receive and store at least one biopotential signal and at least one reference secondary input signal, the motion classification module further configured to perform motion artifact classification for determining motion meta-information comprising a type and/or severity indication about motion phenomena producing artifacts in the biopotential signal that are capable of contaminating the biopotential signal and communicating said motion meta-information to the motion artifact reduction module;

wherein the motion artifact reduction module is configured to select one of a plurality of filtering techniques based on the information received from the motion classification module and perform motion artifact removal by filtering the received biopotential signal using the selected filtering technique;

wherein one or more filter or other motion artifact reduction settings are adjusted to remove the artifacts that result from motion occurring during measurement of the biopotential signals to generate clean signals, wherein an improvement of analysis of the biopotential signals is achieved as a result of using the clean signals to produce an output signal that compensates for the motion, the output signal thereby providing calculated results of the subject's biosigns having improved accuracy;

wherein the motion classification module and the motion artifact reduction module are implemented with software and a programmable processor;

wherein the system is configured to evaluate an effectiveness of at least one algorithm used for motion artifact removal;

wherein the system is further configured to generate feedback information between the motion classification module and the motion artifact reduction module for optimizing performance of the motion artifact classification, the optimizing being automatically selected based on the motion meta-information extracted via the motion artifact classification; and wherein the system produces an output based on the biopotential signals measured, the output comprising treatment data that is utilized to treat the subject, the treatment data being derived as a function of the calculated results.

2. The system of claim 1, wherein the system is further configured to store and process outputs of the motion classification module and the motion artifact reduction module in different periods of time in order to generate said feedback information for optimizing the performance of the motion artifact classification.

3. The system of claim 1, wherein evaluating the effectiveness of at least one algorithm used for motion artifact removal comprises comparing the biopotential signal after motion artifact removal with a reference baseline signal of such biopotential signal.

4. The system of claim 1, wherein the at least one reference secondary input signal is a signal comprising information about one or a combination of contact impedance, contact force, motion acceleration, temperature or humidity.

5. The system of claim 1, wherein the motion classification module is further configured to determine and communicate setting parameters for artifact removal to the motion artifact reduction module.

6. The system of claim 5, wherein the setting parameters comprise an artifact removal technique selection indication and/or coefficients related to a given artifact removal technique and/or signal selection indication for a given artifact removal technique.

7. The system of claim 1, wherein the motion artifact reduction module is further configured to apply, configure, and/or optimize a certain artifact removal technique based on information received from the motion classification module.

8. The system of claim 1, wherein the motion classification module and the motion artifact reduction module are configured for performing one or a combination of classification, statistical analysis, spectral analysis, cross-signal analysis, principal component analysis, independent component analysis, canonical component analysis, adaptive filtering, Bayesian filtering or empirical mode decomposition techniques.

9. The system of claim 1, further comprising a pre-processing module configured to adapt the received signals in order to be processed by the motion classification module and/or a post-processing module configured to adapt the output signals provided by the motion classification module and/or the motion artifact reduction module.

10. A method for the analysis of biopotential signals, comprising, in a system according to claim 1:
receiving and storing at least one biopotential signal;
receiving and storing at least one reference secondary input signal;
performing motion artifact classification for determining motion meta-information comprising a type and/or severity indication about motion phenomena causing motion artifacts in the biopotential signal;
selecting one of a plurality of filtering techniques based on that motion artifact classification;
performing removal of the motion artifacts from the biopotential signal by filtering the biopotential using the selected filtering technique, wherein the performing motion artifact classification and the performing removal of the motion artifacts are implemented with software and a programmable processor;
evaluating the effectiveness of the removal of the motion artifacts from the biopotential signal;
generating feedback information for optimizing performance of the motion artifact classification; and
treating the subject via the output generated based on the biopotential signals measured and the calculated results.

11. The method of claim 10, further comprising storing and processing outputs of the motion classification module and the motion artifact reduction module in different periods of time in order to generate said feedback information for optimizing the performance of the motion artifact classification.

12. The method of claim 10, wherein evaluating the effectiveness of the removal of the motion artifacts from the biopotential signal comprises comparing the biopotential signal after motion artifact removal with a reference baseline signal of such biopotential signal.

13. The method of claim 10, wherein the at least one reference secondary input signal is a signal comprising information about one or a combination of contact impedance, contact force, motion acceleration, temperature or humidity.

14. The method of claim 10, further comprising determining and communicating setting parameters for artifact removal to the motion artifact reduction module, wherein the setting parameters comprise an artifact removal technique selection indication and/or coefficients related to a given artifact removal technique and/or signal selection indication for a given artifact removal technique.

15. The method of claim 10, further comprising applying, configuring, and/or optimizing a certain artifact removal technique based on information received from the motion classification module.

16. The method of claim 10, further comprising performing one or a combination of classification, statistical analysis, spectral analysis, cross-signal analysis, principal component analysis, independent component analysis, canonical component analysis, adaptive filtering, Bayesian filtering or empirical mode decomposition techniques.

17. The system of claim 1 wherein extraction of the clean signals from the biopotential signals containing the artifacts contaminating the biopotential signals is performed based on the meta-information extracted from one or more reference secondary input signals, including electrode-to-tissue impedance, force applied to an electrode, contact force of the electrode, or acceleration of the electrode, and wherein the meta-information comprises signal properties, including standard deviation, slope, and/or higher-order statistics.

18. A system for the analysis of biopotential signals, comprising:
means for receiving at least one biopotential signal;
means for receiving at least one reference secondary input signal;
one or more storage devices that store the at least one biopotential signal and the at least one reference secondary input signal;
means for performing motion artifact classification for determining motion meta-information comprising a type and/or severity indication about motion phenomena causing motion artifacts in the biopotential signal;
means for selecting one of a plurality of filtering techniques based on that motion artifact classification;
means for performing removal of the motion artifacts from the biopotential signal by filtering the biopotential using the selected filtering technique; and
means for evaluating the effectiveness of the removal of the motion artifacts from the biopotential signal;
wherein feedback information is generated, based on at least one output of a motion artifact reduction module and/or a motion classification module for optimizing the performance of the motion artifact classification;

wherein at least the performing removal of the motion artifacts is implemented with software and a programmable processor;

wherein one or more filter or other motion artifact reduction settings are adjusted to remove the artifacts that result from motion occurring during measurement of the biopotential signals to generate clean signals, wherein an improvement of analysis of the biopotential signals is achieved as a result of using the clean signals to produce an output signal that compensates for the motion, the output signal thereby providing calculated results of the subject's biosigns having improved accuracy; and wherein the subject is treated by utilizing an output generated based on the biopotential signals measured, the output comprising treatment data that is derived as a function of the calculated results.

19. The system of claim 18, wherein the biopotential signal receiving means comprises a motion classification module, wherein the reference signal receiving means comprises the motion classification module, wherein the classification performing means comprises the motion classification module, wherein the removal performing means comprises a motion artifact reduction module, wherein the evaluating means comprises the motion artifact reduction module, and wherein the feedback information is generated via the motion artifact reduction module.

20. A non-transitory computer readable medium, comprising computer executable instructions for causing a processor to perform a method for the analysis of biopotential signals, the method comprising:

receiving at least one biopotential signal;

receiving at least one reference secondary input signal;

storing the at least one biopotential signal and the at least one reference secondary input signal;

performing motion artifact classification for determining motion meta-information comprising a type and/or severity indication about motion phenomena causing motion artifacts in the biopotential signal;

selecting one of a plurality of filtering techniques based on that motion artifact classification;

performing removal of the motion artifacts from the biopotential signal by filtering the biopotential using the selected filtering technique, wherein the performing motion artifact classification and performing removal of the motion artifacts are implemented with software and a programmable processor;

evaluating the effectiveness of the removal of the motion artifacts from the biopotential signal;

generating feedback information for optimizing the performance of the motion artifact classification, wherein one or more filter or other motion artifact reduction settings are adjusted to remove the artifacts that result from motion occurring during measurement of the biopotential signals to generate clean signals, wherein an improvement of analysis of the biopotential signals is achieved as a result of using the clean signals to produce an output signal that compensates for the motion, the output signal thereby providing calculated results of the subject's biosigns having improved accuracy; and treating the subject by utilizing an output generated based on the biopotential signals measured, the output comprising treatment data that is derived as a function of the calculated results.

21. The computer-readable medium of claim 20, the method further comprising:

evaluating outputs of the motion artifact removal algorithms with respect to expected signal properties; and building a knowledge database regarding estimated effectiveness of the algorithms, the knowledge database storing information regarding how to optimize motion classification as well as motion artifact reduction.

* * * * *